US010058257B2

(12) United States Patent
Miyazaki et al.

(10) Patent No.: US 10,058,257 B2
(45) Date of Patent: Aug. 28, 2018

(54) MAGNETIC RESONANCE IMAGING APPARATUS AND MAGNETIC RESONANCE IMAGING METHOD

(71) Applicant: TOSHIBA MEDICAL SYSTEMS CORPORATION, Otawara-Shi, Tochigi-Ken (JP)

(72) Inventors: Mitsue Miyazaki, Des Plaines, IL (US); Shigehide Kuhara, Otawara (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 0 days.

(21) Appl. No.: 15/803,381

(22) Filed: Nov. 3, 2017

(65) Prior Publication Data
US 2018/0055380 A1 Mar. 1, 2018

Related U.S. Application Data

(62) Division of application No. 15/415,207, filed on Jan. 25, 2017, now Pat. No. 9,839,366, which is a division
(Continued)

(30) Foreign Application Priority Data

Sep. 18, 2009 (JP) ................. 2009-216890

(51) Int. Cl.
| | |
|---|---|
| *A61B 5/029* | (2006.01) |
| *A61B 5/00* | (2006.01) |
| *G01R 33/385* | (2006.01) |
| *A61B 5/0402* | (2006.01) |

(Continued)

(52) U.S. Cl.
CPC ............ *A61B 5/029* (2013.01); *A61B 5/0037* (2013.01); *A61B 5/0263* (2013.01);
(Continued)

(58) Field of Classification Search
CPC ..................................................... A61B 5/029
See application file for complete search history.

(56) References Cited

U.S. PATENT DOCUMENTS

| | | | |
|---|---|---|---|
| 6,500,123 | B1 | 12/2002 | Holloway et al. |
| 6,782,286 | B2 | 8/2004 | Miyazaki |

(Continued)

FOREIGN PATENT DOCUMENTS

| | | |
|---|---|---|
| CN | 101138497 A | 3/2008 |
| CN | 101259023 A | 9/2008 |

(Continued)

OTHER PUBLICATIONS

Communication of Extended European Search Report dated Dec. 30, 2010, in EP 10161372.7 with Extended European Search Report attached.
(Continued)

*Primary Examiner* — Rochelle Turchen
(74) *Attorney, Agent, or Firm* — Nixon & Vanderhye P.C.

(57) ABSTRACT

An MRI apparatus includes an imaging data acquiring unit and a blood flow information generating unit. The imaging data acquiring unit acquires imaging data from an imaging region including myocardium, without using a contrast medium, by applying a spatial selective excitation pulse to a region including at least a part of an ascending aorta for distinguishably displaying inflowing blood flowing into the imaging region. The blood flow information generating unit generates blood flow image data based on the imaging data.

9 Claims, 21 Drawing Sheets

Related U.S. Application Data of application No. 13/849,316, filed on Mar. 22, 2013, now Pat. No. 9,585,576, which is a division of application No. 12/763,643, filed on Apr. 20, 2010, now Pat. No. 9,474,455.

(51) Int. Cl.
  *A61B 5/026* (2006.01)
  *G01R 33/563* (2006.01)
  *G01R 33/56* (2006.01)
  *G01R 33/54* (2006.01)
  *G01R 33/483* (2006.01)

(52) U.S. Cl.
  CPC .......... *A61B 5/0402* (2013.01); *A61B 5/7271* (2013.01); *A61B 5/742* (2013.01); *G01R 33/385* (2013.01); *G01R 33/5635* (2013.01); *G01R 33/56366* (2013.01); *G01R 33/4833* (2013.01); *G01R 33/543* (2013.01); *G01R 33/5601* (2013.01); *G01R 33/5608* (2013.01)

(56) References Cited

U.S. PATENT DOCUMENTS

| | | |
|---|---|---|
| 6,801,800 B2 | 10/2004 | Miyazaki et al. |
| 7,613,496 B2 | 11/2009 | Miyazaki et al. |
| 2002/0077546 A1 | 6/2002 | Aldefeld et al. |
| 2002/0188197 A1 | 12/2002 | Bishop et al. |
| 2004/0049106 A1 | 3/2004 | Kanazawa |
| 2004/0068175 A1 | 4/2004 | Miyazaki et al. |
| 2004/0162483 A1 | 8/2004 | Kimura |
| 2006/0182362 A1 | 8/2006 | McLain et al. |
| 2007/0038077 A1 | 2/2007 | Wiethoff et al. |
| 2007/0253609 A1 | 11/2007 | Aben |
| 2008/0061780 A1 | 3/2008 | Yamada et al. |
| 2008/0071166 A1 | 3/2008 | Miyazaki |
| 2008/0273782 A1 | 11/2008 | Ichihara |
| 2009/0005670 A1 | 1/2009 | Ichinose et al. |
| 2009/0005673 A1 | 1/2009 | Rehwald et al. |
| 2009/0143666 A1 | 6/2009 | Edelman et al. |
| 2009/0148020 A1 | 6/2009 | Sugiura |
| 2009/0221905 A1 | 9/2009 | Takei |
| 2010/0134107 A1 | 6/2010 | Kitamoto |
| 2011/0071382 A1 | 3/2011 | Miyazaki et al. |
| 2013/0253307 A1 | 9/2013 | Miyazaki |
| 2017/0127952 A1 | 5/2017 | Miyazaki |

FOREIGN PATENT DOCUMENTS

| | | |
|---|---|---|
| JP | 1-299544 | 12/1989 |
| JP | 2001-252263 | 9/2001 |
| JP | 2002-143125 | 5/2002 |
| JP | 2004-242948 | 9/2004 |
| JP | 2005-137558 | 6/2005 |
| JP | 2005-531352 | 10/2005 |
| JP | 2006-198411 | 8/2006 |
| JP | 2008-067857 | 3/2008 |
| JP | 2009-028511 | 2/2009 |
| JP | 2009/201841 A | 9/2009 |
| WO | 2008/136274 A | 11/2008 |

OTHER PUBLICATIONS

Stuber, et al., "Selective Three-Dimensional Visualization of the Coronary Arterial Lumen Using Arterial Spin Tagging," *Magnetic Resonance in Medicine*, Academic Press, Duluth, MN, US, vol. 47, No. 2, Feb. 1, 2002, pp. 322-329, XP002378633, ISSN: 0740-3194, DOI: 10.1002/MRM.10042.

Kanazawa, et al., "Time-Spatial Labeling Inversion Tag (t-SLIT) Using a Selective IR-Tag On/Off Pulse in 2D and 3D Half-Fourier FSE as Arterial Spin Labeling," *Proceedings of the International Society for Magnetic Resonance in Medicine*, 10th Scientific Meeting and Exhibition, Honolulu, Hawaii, USA, May 18-24, 2002, May 4, 2002, p. 140, XP002614067.

Yui, et al.,"Aortic Arch to Intracranial 3D MRA with t-SLIT 3D-SSFP Using a Neurovascular-Attached QD Head SPEEDER Coil," *Proceedings of the International Society for Magnetic Resonance in Medicine*, 12th Scientific Meeting and Exhibition, Kyoto, Japan, May 15-21, 2004, May 1, 2004, p. 2121, XP002614068.

Shimada, et al., "Non-Contrast-Enhanced MR Angiography for Selective Visualization of the Hepatic Vein and Inferior Vena Cava With True Steady-State Free-Precession Sequence and Time-Spatial Labeling Inversion Pulses: Preliminary Results," *Journal of Magnetic Resonance Imaging*, vol. 29, Jan. 22, 2009, pp. 474-479, XP002614069.

Mai, et al.,"A New In Vivo Cardiac Gating Scheme for Perfusion Imaging Studies," *Proceedings of the International Society for Magnetic Resonance in Medicine*, 6th Scientific Meeting and Exhibition, Sydney, Australia, Apr. 18-24, 1998, Apr. 18, 1998, p. 889, XP002614070.

Mai, et al., "Quantification of Steady-State Perfusion Rates Using Flow-Sensitive Alternating Inversion Recovery with an Extra Radiofrequency Pulse (FAIER)," *Proceedings of the International Society for Magnetic Resonance in Medicine*, 6th Scientific Meeting and Exhibition, Sydney, Australia, Apr. 18-24, 1998, Apr. 18, 1998, p. 1215, XP002614071.

Berr, et al., "Cardiac Extraslice Spin Tagging—CEST Perfusion," *Proceedings of the International Society for Magnetic Resonance in Medicine*, 6th Scientific Meeting and Exhibition, Sydney, Australia, Apr. 18-24, 1998, Apr. 18, 1998, p. 923, XP002614072.

Takahashi, et al., "Optimization of Non-Contrast Renal MRA Using a TI-Prep Scan for Time-Spatial Labeling Pulse (Time-SLIP) in 3D Balanced SSFP," *Proceedings of the International Society for Magnetic Resonance in Medicine*, 16th Scientific Meeting and Exhibition, Toronto, Canada, May 3-9, 2008, Apr. 19, 2008, p. 2903, XP002614073.

Shonai, et al., "Improved Arterial Visibility Using Short-Tau Inversion-Recovery (STIR) Fat Suppression in Non-Contrast-Enhanced Time-Spatial Labeling Inversion Pulse (time-SLIP) Renal MR Angiography (MRA)," *Journal of Magnetic Resonance Imaging*, vol. 29, May 26, 2009, pp. 1471-1477, XP002614074.

MRA Time-SLIP, Innervision, 2006, vol. 21, No. 9, pp. 64-65.

Time-SLIP, BBTI 2D BBTI Prep scan, Innervision, 2008, vol. 23, No. 9, pp. 34-38.

Hitoshi, Kanazawa, "Time-Spatial Labeling Inversion Tag (t-SLIT) using a Selective IR-Tag On/Off Pulse in 2D and 3D half-Fourier FSE as Arterial Spin Labeling," ISMRM [CD-ROM], 2002, p. 145.

M. Katoh, "Flow Targeted Coronary MR Angiography: Comparison of Three Different Spin Labeling Techniques," Proceeding of International Society for Magnetic Resonance in Medicine (ISMRM), 2005, vol. 13, p. 709.

Office Action dated May 22, 2013 in U.S. Appl. No. 12/763,643.
Office Action dated Mar. 23, 2015 in U.S. Appl. No. 12/763,643.
Office Action dated Mar. 10, 2015 in JP 2014-139699.
Office Action dated Mar. 10, 2015 in JP 2014-139701.
Office Action dated Jan. 14, 2014 in JP 2010-092235.
JP Office Action dated Jul. 5, 2016 in JP 2014-139700.
CN Office Action dated Feb. 21, 2014 in CN 201210344374.6.
CN Office Action dated Oct. 21, 2014 in CN 201210344374.6.
English translation of JP 2001-252263A (Sep. 2001).

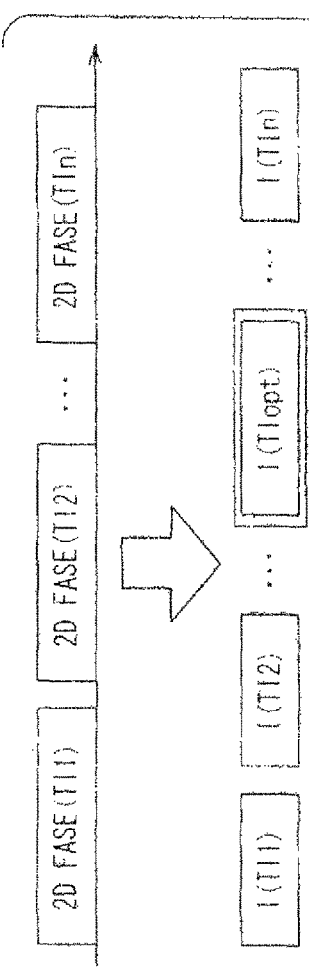
F I G. 13A  T1-PREP SCAN
F I G. 13B  T1-PREP IMAGE
F I G. 13C  BBTI-PREP SCAN
F I G. 13D  BBTI-PREP IMAGE
F I G. 13E  IMAGING SCAN

MAGNETIC RESONANCE IMAGING APPARATUS AND MAGNETIC RESONANCE IMAGING METHOD

CROSS-REFERENCE TO RELATED APPLICATIONS

This application is a division of application Ser. No. 15/415,207 filed Jan. 25, 2017, which is a division of application Ser. No. 13/849,316 filed Mar. 22, 2013 (now issued as U.S. Pat. No. 9,585,576, which is a division of application Ser. No. 12/763,643 filed Apr. 20, 2010 (now issued as U.S. Pat. No. 9,474,455), which claims priority based upon Japanese Patent Application No. 2009-216890 filed Sep. 18, 2009, the entire contents of which are hereby incorporated by reference.

This application is also related to commonly owned Ser. No. 12/946,549 filed Nov. 15, 2010 (now issued as U.S. Pat. No. 8,581,582).

BACKGROUND

1. Technical Field

The subject disclosure relates to MRI (magnetic resonance imaging) that magnetically excites nuclear spins of an object with an RF (radio frequency) signal having the Larmor frequency and reconstructs an image based on NMR (nuclear magnetic resonance) signals generated due to the excitation.

More particularly, the subject disclosure relates to a magnetic resonance imaging apparatus and a magnetic resonance imaging method that can perform MRA (Magnetic Resonance Angiography) for acquiring a blood flow image without using a contrast medium.

2. Description of Related Art

Magnetic Resonance Imaging is an imaging method that magnetically excites nuclear spins of an object set in a static magnetic field with an RF signal having the Larmor frequency and reconstructs an image based on NMR signals generated due to the excitation.

In the field of the magnetic resonance imaging, MRA is known as a method of obtaining an image of a blood flow. An MRA without administration of contrast materials is referred to as a non-contrast MRA (for example, refer to Japanese Publication of Patent Application No. 2001-252263). As the non-contrast MRA, an FBI (fresh blood imaging) method has been devised. In the FBI method, an ECG (electrocardiogram) synchronization to capture a fast blood flow pumped by a heart is performed, and thereby a blood vessel is satisfactorily depicted.

Meanwhile, MR (Magnetic Resonance) perfusion and delayed enhancement are conventionally used for examining an ischemic part and an infarcted part in heart. In the conventional cardiac study, cardiac perfusion and delayed enhance MR imaging are performed under a contrast-enhanced (CE) MRA method in which a patient is given a contrast medium after undergoing medicational stress or exercise stress for the perfusion study.

FIG. 1 shows a cross-section of myocardium for explaining the conventional cardiac study method that uses CE MRA. When dynamic imaging is performed by administering a gadolinium-based contrast medium to a patient, the level of the signal from "tissue A" becomes high. This is because blood flows into "tissue A" which is supplied with blood by normal blood vessels inside the myocardium as shown in FIG. 1. However, in a state in which blood vessels are dilated under medicational stress or exercise stress, a region of low signal level appears as "ischemic part B", because blood flow volume decreases relatively due to stenosed blood vessels. Therefore, the region of the low signal level can be diagnosed as "ischemia is indicated as B". In this way, ischemia test is also called stress perfusion and it can detect an ischemic part as a defect of vascular circulation by administering a contrast medium to a patient under medicational stress or exercise stress.

Additionally, a late delayed enhanced (LDE) technique is known as a method for the diagnosis of infarction. The LDE is a diagnosis method which allows a contrast medium to flow into the myocardium tissue, and thereby diagnoses the part without a function to wash out the contrast medium as the infarction. For example, in "infarction part C" where blood vessels are occluded as shown in FIG. 1, the contrast medium remains within the part C, because the tissue doesn't have the function to wash out the contrast medium. Thus, LDE occurs due to the residual contrast medium, and it enables the detection of "infarction part C" as a region of high signal level as compared to the normal "tissue A" where the contrast medium is washed out.

A cardiac examination is also performed in other diagnostic imaging units and its results are displayed in various display methods. For example, technology to display a myocardium layer of different cross-sections by using cardiac CT image data acquired with X-ray CT (computed tomography) apparatus is known. Also, technology to display a cross-sectional image of myocardium in a bulls-eye method by using cardiac 3-dimensional image data acquired using ultrasonograph (US) is known (for example, refer to the Japanese Publications of Patent Application Nos. 2006-198411 and 2005-531352).

However, in the conventional cardiac examination using an MRI apparatus, ischemic and infarct parts are diagnosed by performing dynamic imaging after injection of gadolinium-based contrast materials under influence of medicational stress or exercise. Therefore, imaging timing is restricted to the period where contrast medium is washed-out in the normal tissue and still in the infarction area after administering a contrast medium, otherwise sufficient contrast can not be obtained. Thus, it has a limit in terms of temporal resolution as a problem. Additionally, spatial resolution also degrades due to the restriction of time resolution. Under the aforementioned technical background, there is a problem that image quality varies and diagnosis varies among readers.

Moreover, the relationship between the gadolinium-based contrast medium and Nephrogenic Systemic Fibrosis (NSF) is concerned due to a black-box warning from the FDA (Food and Drug Administration). Furthermore, in stress perfusion test, risk of medication such as adenosine and dipyridamole is also a huge concern. The aforementioned problems apply to a case in which CE MRA imaging is acquired for various imaging regions.

BRIEF SUMMARY

The present disclosure aims to provide MRI technology which can safely acquire "MRA imaging region including a heart" and "blood flow information based on the MRA image" with satisfactory time resolution and spatial resolution.

The content of the exemplary embodiments will be described per each aspect as follows:

(1) According to one aspect of a magnetic resonance imaging apparatus of the disclosure, the magnetic resonance imaging apparatus comprises an imaging data acquiring unit, a blood flow image generating unit, and a cardiac function analysis unit.

The imaging data acquiring unit acquires a plurality of 3-dimensional imaging data corresponding to mutually different traveling time of inflowing blood flowing into an imaging region including myocardium in synchronization with a heartbeat without using a contrast medium, by applying a spatial selective excitation pulse plural times for distinguishably displaying the inflowing blood and by changing time from application timing of the spatial selective excitation pulse to acquisition timing of the plurality of imaging data.

The blood flow image generating unit generates a plurality of blood flow image data corresponding to the mutually different traveling time of the inflowing blood based on the plurality of imaging data.

The cardiac function analysis unit acquires blood flow information indicating cardiac function of the myocardium based on the plurality of blood flow image data.

(2) According to another aspect of a magnetic resonance imaging apparatus of the exemplary embodiments, the magnetic resonance imaging apparatus comprises an imaging data acquiring unit and a blood flow information generating unit.

The imaging data acquiring unit acquires at least one of imaging data from an imaging region including the myocardium without using a contrast medium, by applying a spatial selective excitation pulse to a region including at least a part of an ascending aorta for distinguishably displaying inflowing blood flowing into the imaging region.

The blood flow information generating unit generates at least one of blood flow image data based on the imaging data.

(3) A magnetic resonance imaging method of the exemplary embodiments comprises the steps of: (a) acquiring imaging data from an imaging region including the myocardium without using a contrast medium, by applying a spatial selective excitation pulse to a region including at least a part of an ascending aorta (cardiac aorta) for distinguishably displaying inflowing blood flowing into the imaging region, and (b) generating blood flow image data based on the imaging data.

According to the magnetic resonance imaging apparatus or the magnetic resonance imaging method configured as described above, MRA image data of an imaging region including heart and blood flow information based on the MRA images can be acquired safely with satisfactory time resolution and spatial resolution.

BRIEF DESCRIPTION OF THE DRAWINGS

In the accompanying drawings:

FIGS. 13A-E are diagrams for explaining the method of determining TI and BBTI set as imaging conditions in the imaging condition setting unit 40 shown in FIG. 3;

DESCRIPTION OF PREFERRED EMBODIMENTS

A magnetic resonance imaging apparatus and a magnetic resonance imaging method according to embodiments of the exemplary embodiments will be described with reference to the accompanying drawings.

(Configuration and Function)

Figure 1:
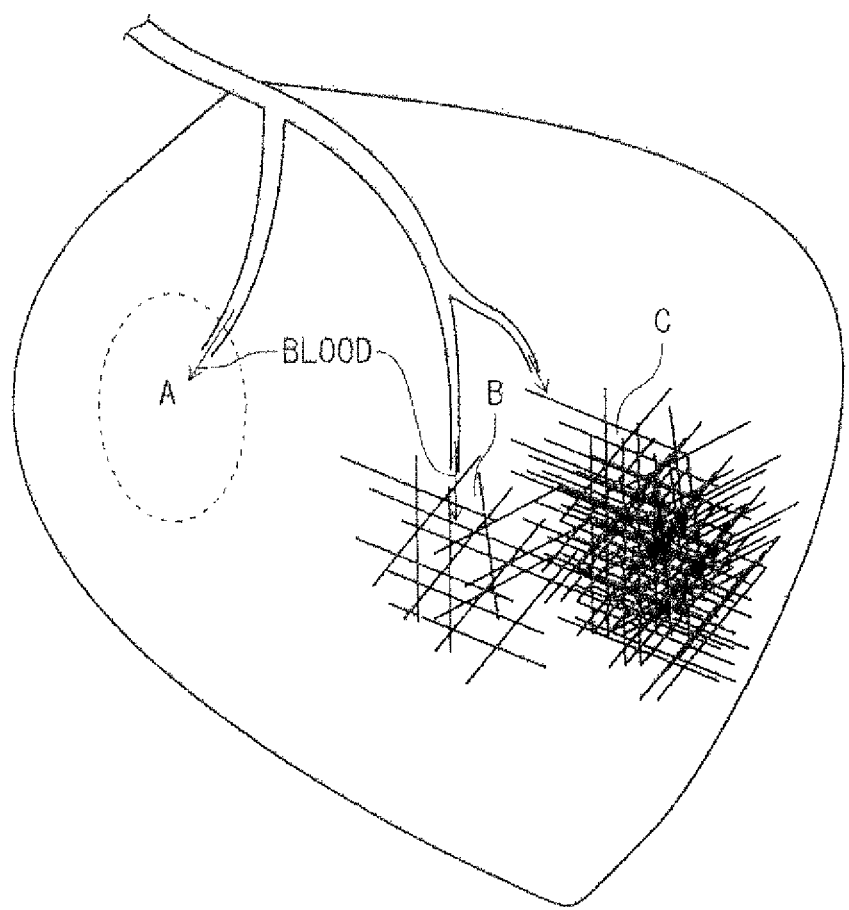
FIG. 1 is a cross-sectional diagram of myocardium for explaining a cardiac testing method using conventional contrast-enhanced (CE) MRA.
Figure 2:
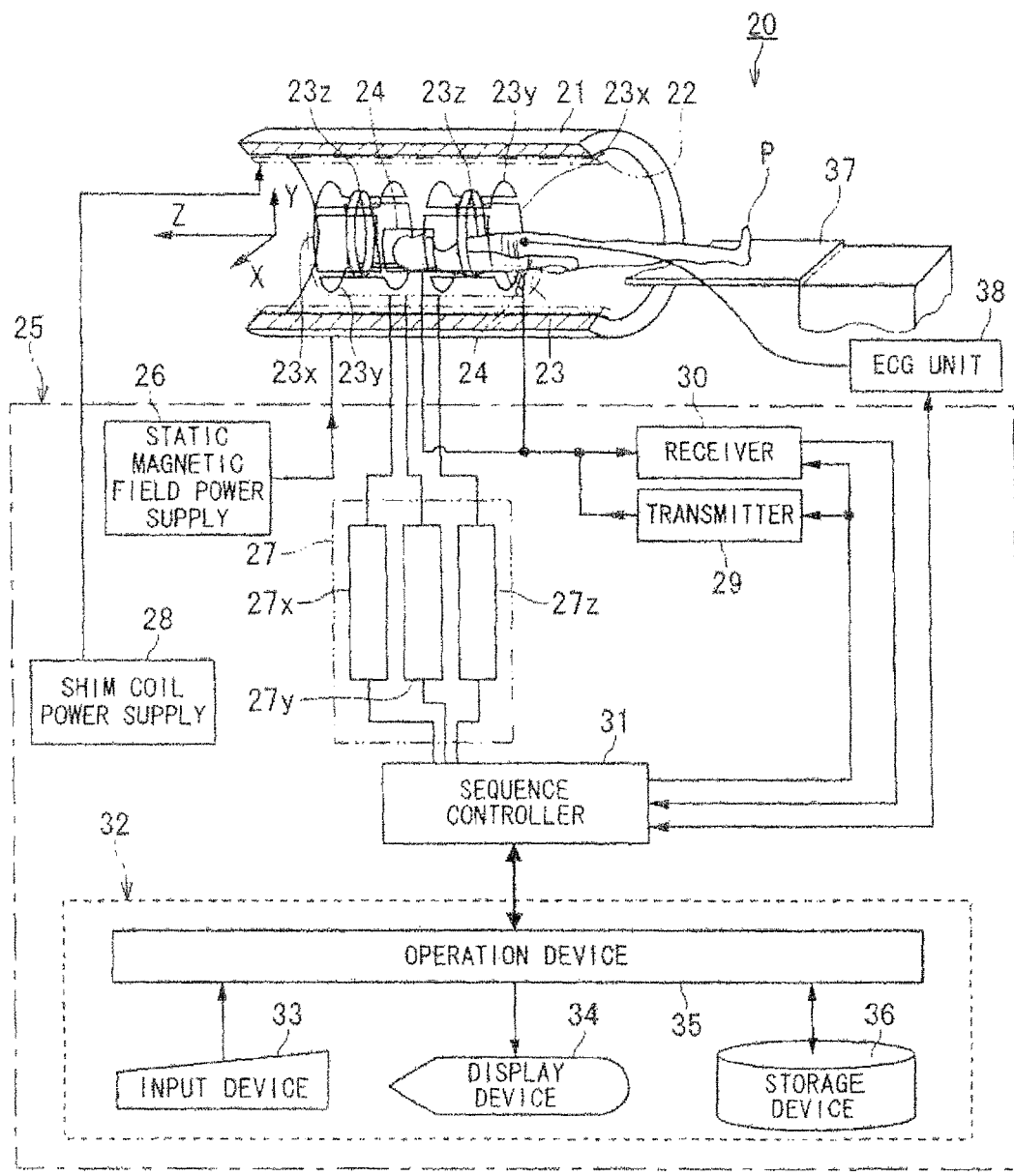
FIG. 2 is a block diagram showing a magnetic resonance imaging apparatus according to one embodiment of the present disclosure.

FIG. 2 is a block diagram showing a magnetic resonance imaging apparatus according to one embodiment of the present disclosure.

A magnetic resonance imaging apparatus 20 includes a cylinder-shaped static magnetic field magnet 21 for generating a static magnetic field, a cylinder-shaped shim coil 22 arranged inside the static magnetic field magnet 21, a gradient coil 23 and RF coils 24.

The magnetic resonance imaging apparatus 20 also includes a control system 25. The control system 25 includes a static magnetic field power supply 26, a gradient magnetic field power supply 27, a shim coil power supply 28, a transmitter 29, a receiver 30, a sequence controller 31 and a computer 32. The gradient magnetic field power supply 27 of the control system 25 includes an X-axis gradient magnetic field power supply 27x, a Y-axis gradient magnetic field power supply 27y and a Z-axis gradient magnetic field power supply 27z. The computer 32 includes an input device 33, a display device 34, an operation device 35 and a storage device 36.

The static magnetic field magnet 21 is electrically connected to the static magnetic field power supply 26 and has a function to generate a static magnetic field in an imaging region by using electric current supplied from the static magnetic field power supply 26. The static magnetic field magnet 21 includes a superconductivity coil in many cases. The static magnetic field magnet 21 gets electric current from the static magnetic field power supply 26 which is electrically connected to the static magnetic field magnet 21 at excitation. However, once excitation has been made, the static magnetic field magnet 21 is usually isolated from the static magnetic field power supply 26. The static magnetic field magnet 21 may include a permanent magnet which makes the static magnetic field power supply 26 unnecessary.

The cylinder-shaped shim coil 22 is coaxially arranged inside the static magnetic field magnet 21. The shim coil 22 is electrically connected to the shim coil power supply 28. The shim coil power supply 28 supplies electric current to the shim coil 22 so that the static magnetic field becomes uniform.

The gradient coil 23 includes an X-axis gradient coil 23x, a Y-axis gradient coil 23y and a Z-axis gradient coil 23z. Each of the X-axis gradient coil 23x, the Y-axis gradient coil 23y and the Z-axis gradient coil 23z is cylinder-shaped and arranged inside the static magnetic field magnet 21. A bed 37 is arranged inside the gradient coil 23 and the area inside the gradient coil 23 is an imaging area. The bed 37 supports an object (e.g., a patient) P. The RF coils 24 include a WBC (whole body coil) built in the gantry for transmission and reception of RF signals and local coils arranged around the bed 37 or the object P for reception of RF signals.

The gradient coil 23 is electrically connected to the gradient magnetic field power supply 27. The X-axis gradient coil 23x, the Y-axis gradient coil 23y and the Z-axis gradient coil 23z of the gradient coil 23 are electrically connected to the X-axis gradient magnetic field power supply 27x, the Y-axis gradient magnetic field power supply 27y and the Z-axis gradient magnetic field power supply 27z of the gradient magnetic field power supply 27 respectively.

The X-axis gradient magnetic field power supply 27x, the Y-axis gradient magnetic field power supply 27y and the Z-axis gradient magnetic field power supply 27z supply electric currents to the X-axis gradient coil 23x, the Y-axis gradient coil 23y and the Z-axis gradient coil 23z respectively so as to generate gradient magnetic field Gx in the X-axis direction, gradient magnetic field Gy in the Y-axis direction and gradient magnetic field Gz in the Z-axis direction in the imaging area.

The RF coils 24 are electrically connected to the transmitter 29 and/or the receiver 30. The transmission RF coil 24 has a function to transmit a RF signal given from the transmitter 29 to the object P. The reception RF coil 24 has a function to receive an NMR signal generated due to excited nuclear spin inside the object P by the RF signal and give the received NMR signal to the receiver 30.

The sequence controller 31 of the control system 25 is electrically connected to the gradient magnetic field power supply 27, the transmitter 29 and the receiver 30. The sequence controller 31 has a function to storage sequence information describing control information needed in order to make the gradient magnetic field power supply 27, the transmitter 29 and the receiver 30 drive. The aforementioned control information includes motion control information, such as intensity, impression period and impression timing of the pulse electric current which should be impressed to the gradient magnetic field power supply 27. The sequence controller 31 also has a function to generate gradient magnetic fields Gx, Gy and Gz in the X-axis, Y-axis and Z-axis directions and RF signals by driving the gradient magnetic field power supply 27, the transmitter 29 and the receiver 30 according to a predetermined sequence stored.

The sequence controller 31 is also configured to receive raw data, which are complex data obtained through the detection of an NMR signal and A/D conversion to the NMR signal detected in the receiver 30, and input the raw data to the computer 32.

Therefore, the transmitter 29 has a function to give an RF signal to the transmission RF coil 24 in accordance with the control information provided from the sequence controller 31. The receiver 30 has a function to generate raw data which are digitized complex number data obtained by detecting an NMR signal given from the reception RF coil 24, performing predetermined signal processing to the NMR signal detected, and performing A/D conversion to the NMR signal after the predetermined signal processing. The receiver 30 also has a function to give the generated raw data to the sequence controller 31.

In addition, the magnetic resonance imaging apparatus 20 comprises an ECG unit 38 for acquiring an ECG (electrocardiogram) signal of the object P. The ECG signal detected by the ECG unit 38 is outputted to the computer 32 through the sequence controller 31.

Note that a PPG (peripheral pulse gating) signal representing a cardiac beat as pulse wave information may be acquired instead of the ECG signal representing a cardiac beat as heart rate information. A PPG signal is acquired by detecting a pulse wave of, e.g., a tip of a finger as an optical signal. When a PPG signal is acquired, a PPG signal detection unit is provided with the magnetic resonance imaging apparatus 20. Hereinafter, a case of acquiring the ECG signal will be described.

The computer 32 obtains various functions by the operation device 35 executing some programs stored in the storage device 36 of the computer 32. Alternatively, some specific circuits having various functions may be provided with the magnetic resonance imaging apparatus 20 instead of using some of the programs.

Figure 3:
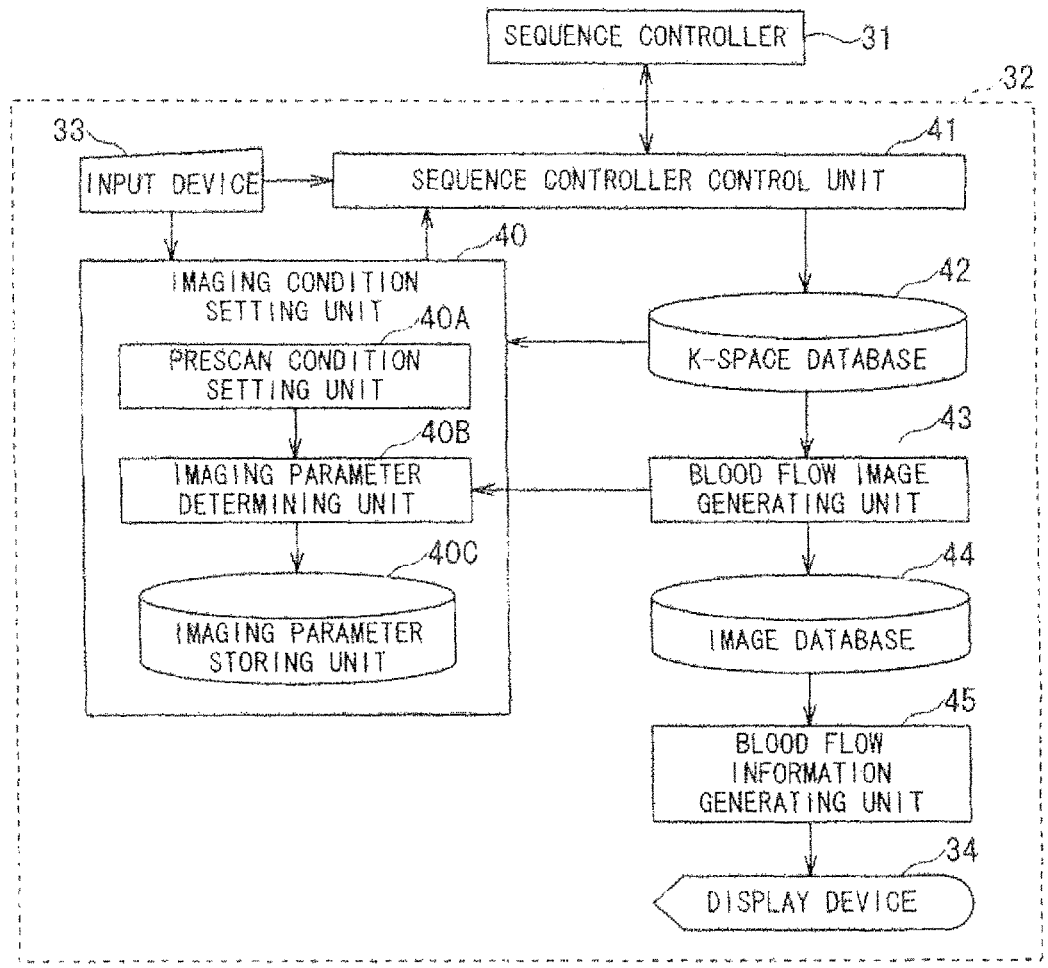
FIG. 3 is a functional block diagram of the computer 32 shown in FIG. 2.

FIG. 3 is a functional block diagram of the computer 32 shown in FIG. 2.

The computer 32 functions as an imaging condition setting unit 40, a sequence controller control unit 41, a k-space database 42, a blood flow image generating unit 43, an image database 44 and a blood flow information generating unit 45. The imaging condition setting unit 40 comprises a prescan condition setting unit 40A, an imaging parameter determining unit 40B and an imaging parameter storing unit 40C.

The imaging condition setting unit 40 has a function to set imaging conditions including a pulse sequence based on instructions from the input device 33 and to provide the set imaging conditions to the sequence controller control unit 41. Additionally, the imaging condition setting unit 40 has a function to set a pulse sequence to acquire a blood flow image on a cross-section of myocardium by labeling (tagging) blood flowing into an imaging region under ECG synchronization without using a contrast medium. The imaging condition setting unit 40 also has a function to set a plurality of pulse sequences to acquire a plurality of blood flow images, each of which is indicative of mutually different traveling time of labeled blood. Note that the term "label" or "labeling" as used herein is synonymous with "tag" or "tagging", respectively.

As an imaging sequence for acquiring data from an imaging region including a plurality of cross-sections of myocardium, for example, a three-dimensional (3D)-fast spin echo (FSE) sequence, a 3D-fast asymmetric spin echo or fast advanced spin echo (FASE) sequence, a 3D steady state free precession (SSFP) sequence, an echo planar imaging (EPI) sequence and a radial data acquiring sequence can be used.

The FASE sequence is an FSE-type sequence which utilizes a half-Fourier method.

The radial data acquiring sequence includes a Periodically Rotated Overlapping Parallel Lines with Enhanced Reconstruction (PROPELLER) sequence which rotates a plurality of data acquiring lines.

The SSFP sequence has different versions such as a balanced SSFP sequence (or a true SSFP sequence). The balanced SSFP sequence and the true SSFP sequence are suitable for fast data acquisition because of their high efficiency of data acquisition.

The FBI method is known as non-contrast-enhanced MRA. The FBI method is a non-contrast-enhanced MRA which uses a sequence such as a FASE sequence to acquire echo data repeatedly every plural heartbeats at the timing delayed by a predetermined time from a trigger signal. This trigger signal is synchronized with a reference wave, such as an R wave, indicative of a cardiac time phase of the object P.

According to the FBI method, a transverse relaxation (T2) component of magnetization in blood recovers with elapse of plural heartbeats, thereby water (blood) weighted imaging, in which the T2 magnetization component of blood is enhanced, can be obtained as a blood vessel image. Moreover, three dimensional imaging for acquiring echo data (volume data) for predetermined slice encode amounts is performed in the FBI method.

Furthermore, imaging conditions for labeling blood are set in order to depict blood flowing from an aorta into an imaging region inside the heart satisfactorily. As one of labeling methods, a Time-SLIP (Time Spatial Labeling Inversion Pulse) method, in which a plurality of labeling pulses is applied, is known. Hereinafter, the time-SLIP method will be described as an example of labeling methods.

In the time-SLIP method, a time-SLIP pulse for labeling is applied in accordance with the time-SLIP sequence and blood flowing into an imaging region is labeled. That is, the time-SLIP sequence is an imaging sequence which applies an arterial spin labeling (ASL) pulse for labeling blood flowing into an imaging section so that the labeled blood is selectively depicted or suppressed. According to this time-SLIP sequence, signal intensities of only blood reaching the imaging region after TI (inversion time) can be selectively emphasized or suppressed. The time-SLIP pulse is applied after a certain delay time from an R wave of an ECG signal. In this case, imaging is performed under ECG synchronization.

In the time-SLIP sequence, "a spatial non-selective inversion pulse (region non-selective inversion pulse)" and "a spatial selective inversion pulse (region selective inversion pulse)" are used. The spatial non-selective inversion pulse can be switched on/off. The time-SLIP sequence includes at least the spatial selective inversion pulse. That is, there are two cases for the time-SLIP sequence. In one case, the time-SLIP sequence consists of the spatial selective inversion pulse(s) only. In the other case, the time-SLIP sequence includes both the spatial non-selective inversion pulse(s) and the spatial selective inversion pulse(s).

The spatial selective inversion pulse can be set arbitrarily independent of an imaging region. When blood flowing into an imaging region is labeled with the spatial selective inversion pulse, signal intensity at the part to which the blood reaches after BBTI becomes strong. Note that when the spatial non-selective inversion pulse is set to off, signal intensity at the part to which blood reaches after BBTI becomes weak. Therefore, a moving direction and a distance of blood movement can be understood.

Figure 4:
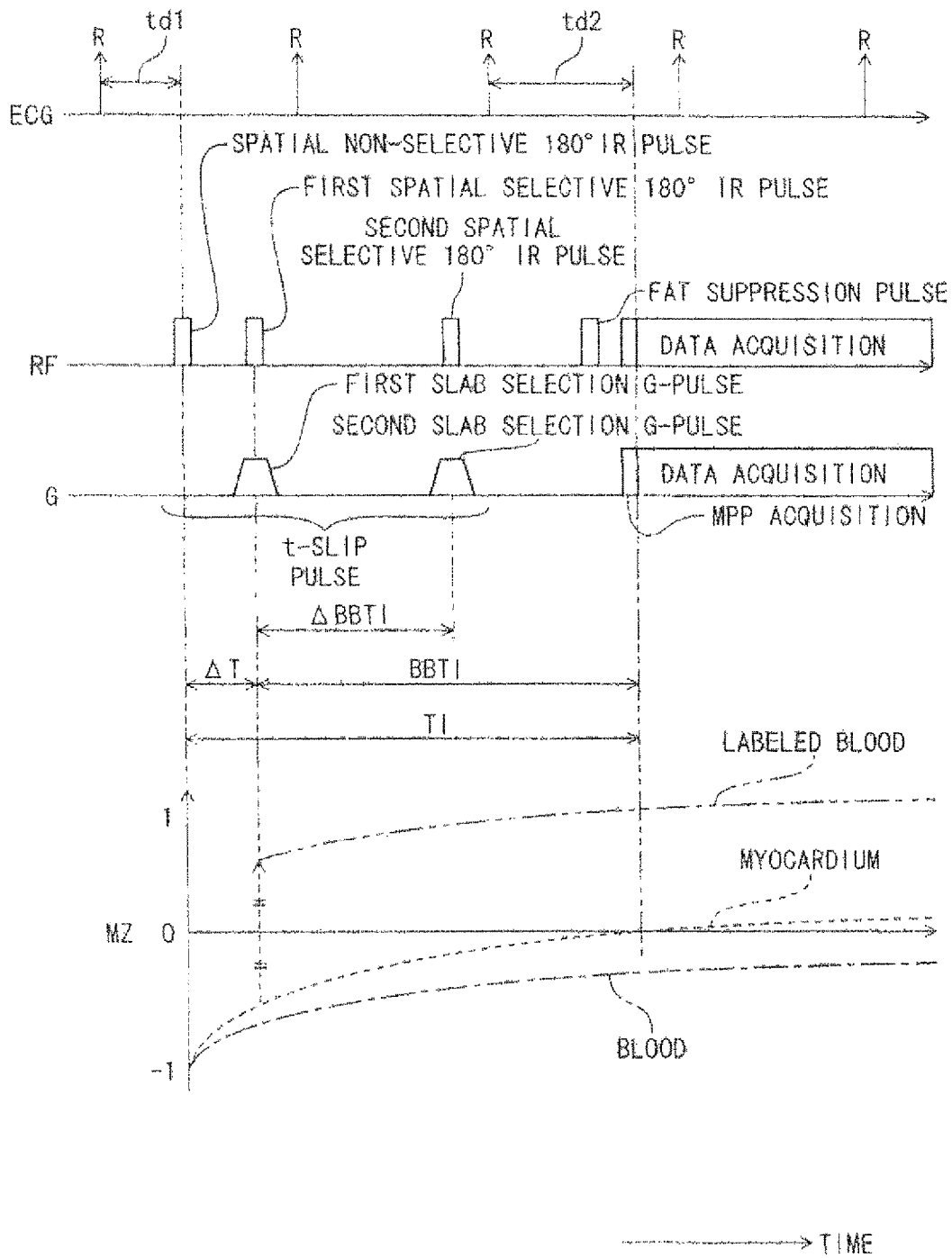
FIG. 4 is a timing chart showing an example of a time-spatial labeling pulse (time-SLIP) sequence set in the imaging condition setting unit 40 shown in FIG. 3.

FIG. 4 is a timing chart showing an example of the time-SLIP sequence set in the imaging condition setting unit 40 shown in FIG. 3. In FIG. 4, the abscissa axis indicates passing time t. Additionally, ECG, RF, G and Mz in FIG. 4 indicate an R wave as an ECG trigger, an RF signal, a gradient magnetic field pulse and longitudinal magnetization component, respectively. Also, td1 is a time period (delay time) from the time of an R wave to the time of applying a spatial non-selective 180° IR (inversion recovery) pulse. Additionally, td2 is a time period (delay time) from the time of an R wave just before the starting time of data acquisition to the time of starting the data acquisition.

As shown in FIG. 4, the spatial non-selective 180° IR pulse is applied at the timing delayed by the predetermined delay time td1 from the time of the R wave, in synchronization with the R wave of the ECG signal. Thereby longitudinal magnetization component Mz of myocardium and blood inside the object P inverts. That is, both of the longitudinal magnetization components Mz of the myocardium and the blood become −1.

Next, the first and second 180° spatial selective IR pulses are applied at a different timing each other to a slab selected as a labeling region. Note that the application timing of the first spatial selective 180° IR pulse is ΔT after the application timing of the spatial non-selective 180° IR pulse. Additionally, in order to select a slab for labeling, the first and second 180° slab-selective excitation gradient magnetic field pulses are respectively applied at the same timing as the application timing of the first or second spatial selective 180° IR pulse. Thereby, longitudinal magnetization component Mz of blood inside the labeling region selectively inverts after recovering by the quantity according to the time interval between the spatial non-selective 180° IR pulse and the spatial selective 180° IR pulse. That is, the blood inside the labeling region is labeled.

Note that in FIG. 4, the longitudinal magnetization component Mz of the blood inside the labeling region inverted by the first spatial selective 180° IR pulse is shown as a two-dot chain line, whereas the Mz of the blood inverted by the second spatial selective 180° IR pulse is omitted. This is because FIG. 4 becomes complicated if both of them are shown. Meanwhile, the longitudinal magnetization component Mz of blood outside the labeling region is maintained as a negative value without being inverted. That is, the first and second spatial selective 180° IR pulses function as a labeling pulse.

Then, an imaging sequence is started at a timing BBTI after the application timing of the 180° spatial non-selective pulse (that is, at a timing BBTI (Black Blood Traveling Time) after the application timing of the first spatial selective 180° IR pulse), and data acquisition of the imaging region including the myocardium part is started.

Note that it is preferable to perform the data acquisition at a cardiac time phase of the same diastole consistently, because the myocardium is always in motion. Then, the delay time td1 and td2 of ECG synchronization are set so that the data acquisition is performed at an appropriate cardiac time phase at diastole.

More specifically, the heart is the most suitable for data acquisition in terminal phase at diastole, because its state in terminal phase at diastole is the closest to static condition due to smaller heartbeat. In the exemplary embodiments, images are respectively acquired for mutually different BBTIs by changing BBTI as will be mentioned later, whereas it is impossible to synchronize the start timing of the data acquisition with the terminal phase at diastole by merely increasing BBTI each time of the data acquisition.

It is desirable to control the delay time td1, td2, and the relationship between the labeling pulse and the region non-selective pulse by means of satisfying the following two conditions (a) and (b), when BBTI is increased: (a) is to synchronize the start timing of the data acquisition with the terminal phase of diastole consistently (through the entire data acquisition), and (b) is to start the data acquisition when the longitudinal magnetization component Mz of the unlabeled myocardium is zero (when the background signal is inhibited).

In order to satisfy the conditions (a) and (b), the exemplary embodiments enable control of BBTI and inhibition of the background signal independently by using the following equations (1) and (2):

$$Td1+\Delta T+BBTI=n \times RR+td2 \quad (1)$$

$$\Delta T+BBTI=TI \quad (2)$$

In the equation (1), RR is a time interval between an R wave and the next R wave, "n" is counting number equal to or larger than 1 (for example, up to 3). FIG. 4 corresponds to the case where n=2. In the equation (2), TI is a physical value determined by longitudinal relaxation time of the myocardium, and is constant.

Then, in this embodiment, RR is measured based on an ECG signal, then "n" is determined, and then the delay time td2 is determined so as to synchronize the start timing of the data acquisition with the terminal phase of diastole. When the delay time td2 is determined, the delay time td1 is unambiguously determined based on the equation (1). Next, $\Delta T$ and BBTI are determined based on the equation (2) so that the data acquisition starts at the same timing as the longitudinal magnetization component Mz of the unlabeled myocardium becomes zero.

Here, in order to prolong reaching distance of blood, it is necessary to extend BBTI. Therefore, BBTI may be set longer than TI by setting the sign of TI negative. That is, the spatial selective 180° IR pulse may be applied before the spatial non-selective 180° IR pulse.

Note that a cyclic period of one heartbeat is not always the same value, but changes. Thus, it is preferable to change a pulse sequence appropriately according to the change in heartbeats. Specifically, RR for the target of the data acquisition is estimated based on data of ECG signal, a plurality of RRs prior to the RR for the target of the data acquisition, and so on. Then, the delay time td2 is controlled (adjusted) based on the estimated value of RR dynamically or in real-time. In this control (adjustment), it is preferable to avoid performing the data acquisition or to correct the delay time td2 to a value shorter than the estimated value of the RR for the target of the data acquisition, when the estimated value of the RR is extremely short. This is because in the case of the delay time td2 longer than the RR for the target of the data acquisition, the data acquisition may be performed in systole and this cardiac time phase is not appropriate for data acquisition due to larger motion of the heart.

Moreover, a fat suppression pulse such as a fat-saturation pulse, a SPIR (spectral pre-saturation with inversion recovery) pulse and so on is applied before the data acquisition as shown in FIG. 4.

In the case of the FBI method, the period of the data acquisition extends for plural heartbeats. Additionally, because the data acquisition is performed without using a contrast medium, there is no time limit. Therefore, an imaging sequence for performing 3-dimensional data acquisition with high resolution can be used.

Note that TI and BBTIs can be set independently of each other. That is, although a time interval $\Delta T$ between a spatial non-selective 180° IR pulse and a spatial selective 180° IR pulse is almost zero in the conventional art, the time interval $\Delta T$ is changeable in the exemplary embodiments. Though the time interval $\Delta T$ can be set instead of TI or BBTIs, hereinafter, the case of setting TI and BBTIs will be explained.

The longitudinal magnetization components Mz of the myocardium and the unlabeled blood in the imaging region recover after the application of the spatial non-selective 180° IR pulse, as shown in FIG. 4. Then, it is desirable to determine TI so that the data acquisition is started at the same timing as both of "the absolute value of the longitudinal magnetization component Mz of the myocardium functioning as background" and "the absolute value of the longitudinal magnetization component Mz of the unlabeled blood" are equal to or less than a predetermined value and both are approximately zero. Thereby, unnecessary signals from the unlabeled blood and the myocardium functioning as a background can be inhibited, whereas signal from the labeled blood can be selectively emphasized.

However, recovery rate of the longitudinal magnetization component Mz of the myocardium is different from that of blood as shown in FIG. 4. Then, TI is determined in order for the data acquisition to start at the timing when the longitudinal magnetization component Mz of the myocardium becomes approximately zero. At the same time, the signal from the unlabeled blood can be suppressed by performing data processing. Thereby, unnecessary signals from the unlabeled blood and the myocardium can be inhibited more sufficiently.

The process of eliminating the signals from the unlabeled blood can be performed in blood flow image generating unit 43 as discussed later. Specifically, magnetic resonance signals are complex signals. Therefore, when "real image reconstruction processing" is performed by using real parts (not absolute value) of the magnetic resonance signals, the magnetic resonance signals from the unlabeled blood become low in signal level in image data due to their negative value. Thus, when image data is displayed with luminance according to data values, a labeled blood part with high signal level is displayed with high luminance, whereas the unnecessary unlabeled blood part is displayed with low luminance. Moreover, it is possible to display only the labeled blood selectively whitely as white blood, because signal values from the myocardium are approximately zero.

Moreover, it is possible to make "canonicalized signals of negative value from the unlabeled blood"−1 by applying cosine filter to the acquired data. Thereby, it is possible to make the unlabeled blood part black in the image data displayed with luminance.

Additionally, BBTI can be set so that BBTI extends for plural heartbeats. In order to achieve this, BBTI can be set longer than TI, that is, ΔT<0. When the spatial selective 180° IR pulse is applied, the labeled blood in the labeling region moves into the imaging region after elapse of BBTI. Then, out of signals acquired by the data acquisition, the signal of the labeled blood is especially emphasized. Therefore, if BBTI can be set longer, blood traveling for a longer distance can be emphasized.

The maximum value of settable BBTI can be increased, when the spatial selective 180° IR pulse is applied plural times. That is, when the labeling pulse is applied to the labeling region plural times, quantity of the labeled blood increases and thereby the maximum value of settable BBTI becomes longer. In the example shown in FIG. 4, two spatial selective 180° IR pulses are applied. That is, the second spatial selective 180° IR pulse is applied after the application of the first spatial selective 180° IR pulse.

It is desirable to set ΔBBTI so that the flow of the labeled blood continues uninterruptedly. For example, the maximum value of settable BBTI can be doubled theoretically, if the second spatial selective 180° IR pulse is applied "to the same region as the region applied with the first spatial selective 180° IR pulse" at the timing when all of the blood labeled by the first spatial selective 180° IR pulse flows out of the labeling region. Note that the region to which the second spatial selective 180° IR pulse is applied may be the same as or different from the region to which the first spatial selective 180° IR pulse is applied (both cases can be used in the exemplary embodiments). It is desirable to make the flow of labeled blood consecutive by, for example, setting "the application region of the second spatial selective 180° IR pulse" to "a part of the application region of the first spatial selective 180° IR pulse which is imaging region-side".

Moreover, single or plural MPP (motion probing pulse) as NMR signals for monitoring in an RMC (real-time motion correction) method can be acquired before data acquisition, if needed. The RMC method is a method correcting "a target region for imaging data" and "acquired data" in real-time so that influence of respiratory motion is eliminated by acquiring the MPP with ECG-synchronization generally and using motion quantity measured based on the MPP. The imaging condition setting unit 40 has the function of correcting an imaging data acquisition region based on the RMC method.

The MPP is acquired from a region including, e.g., a diaphragm "with phase encode quantity smaller than that of the imaging data" or "without applying phase encoding gradient magnetic field". Then, the position of the diaphragm regarding a body axial direction at the time of the MPP acquisition can be detected as respiration level based on signals acquired by performing 1D (one-dimensional) FT (Fourier Transformation) on the MPP. Thereby, variation (fluctuation) from a reference value of respiratory level can be determined as respiratory motion quantity (motion quantity caused by respiration). Moreover, the influence of the respiratory motion can be suppressed, if the data acquisition region is moved by the distance corresponding to the respiratory motion quantity.

Additionally, it is possible to visualize time change of the respiratory level and avoid performing data acquisition, when the respiratory level goes out of acceptable level. Moreover, phase correction and positional correction of imaging data may be performed according to the respiratory motion quantity as post-processing for eliminating the influence of the respiratory motion.

Note that the data acquisition may be performed under the state of arrested respiration by making the object P do breath hold with or without the use of the RMC.

Next, another example of the time-SLIP sequence will be explained.

Generally, BBTI value is from 1200 ms (milliseconds) to 1400 ms and TI value is about 600 ms in many cases. Therefore, in the case of the time-SLIP sequence shown in FIG. 4, BBTI is longer than TI in many cases (BBTI>TI). Then, long BBTI can be set with inhibition of unnecessary signals in the case of applying the spatial selective 180° IR pulse after the application of the spatial non-selective 180° IR pulse, when a 180° imaging region selective IR pulse inverting the longitudinal magnetization component Mz of the myocardium and blood in the imaging region is applied after the application of the spatial selective 180° IR pulse for exciting the labeling region.

Figure 5:
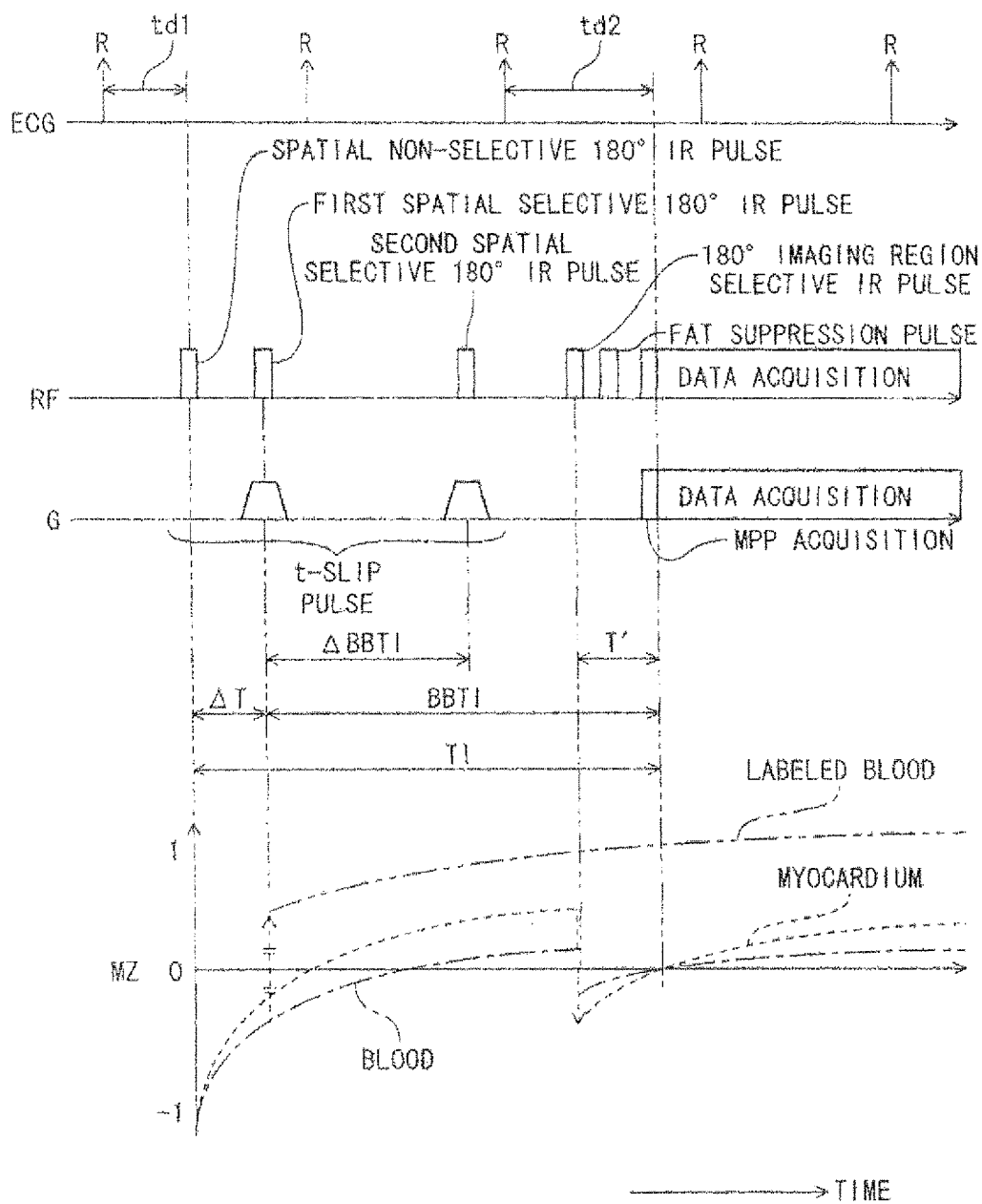
FIG. 5 is a timing chart showing another example of a time-SLIP sequence set in the imaging condition setting unit 40 shown in FIG. 3.

FIG. 5 shows another example of time-SLIP sequence set in the imaging condition setting unit 40 shown in FIG. 3.

The abscissa axis in FIG. 5 indicates elapsing time t. In FIG. 5, ECG, RF, G, and Mz indicate R wave as ECG trigger, an RF signal, a gradient magnetic field pulse, and a longitudinal magnetization component respectively. Additionally, td1 is a delay time from "the R wave time" to "the application time of the spatial non-selective 180° IR pulse". Also, td2 is a delay time from "the R wave time just before the starting time of the data acquisition" to "the starting time of the data acquisition" (the same as FIG. 4).

As shown in FIG. 5, the longitudinal magnetization components of the myocardium and blood in the imaging region can be inverted again by applying the 180° imaging region selective IR pulse, if the longitudinal magnetization components of both myocardium and blood in the imaging region have recovered to a positive value before the labeled blood flows into the imaging region. In this case, the timing, when the longitudinal magnetization components of both myocardium and unlabeled blood become zero simultaneously, appears. This is because the recovery rate of the longitudinal magnetization component Mz of the myocardium is faster than that of the unlabeled blood.

Then, it is desirable to determine the time interval T' from the application time of the 180° imaging region selective IR pulse to the starting time of the data acquisition so that the data acquisition is started at the timing when the longitudinal magnetization components of both myocardium and unlabeled blood become zero. Thereby, signals from the labeled blood can be acquired with high intensity, inhibiting signals from the myocardium and the unlabeled blood sufficiently. Furthermore, BBTI extending for 3RR, which is longer than 2RR, can be set.

Note that even if the longitudinal magnetization component Mz of the unlabeled blood has not recovered to a positive value, the longitudinal magnetization component Mz of dominant myocardium can be inverted to a negative value by applying the 180° imaging region selective IR pulse when the absolute value of the longitudinal magnetization component Mz of the unlabeled blood is small enough to be ignored. Therefore, the signal from the myocardium can be inhibited, even if BBTI is shorter than 2RR.

Next, a setting method of the labeling region of blood will be explained.

The labeling region can be set to a part where a coronary artery providing the myocardium with blood branches from an aorta. More specifically, as vessels providing the myocardium with blood, there are an RCA (Right Coronary Artery), an LMT (Left Main Coronary Trunk), an LCX (Left Circumflex Artery), and an LAD (Left Anterior Descending Artery). Blood of an arbitrary vessel providing the myocardium with blood is the target for labeling.

Figure 6:
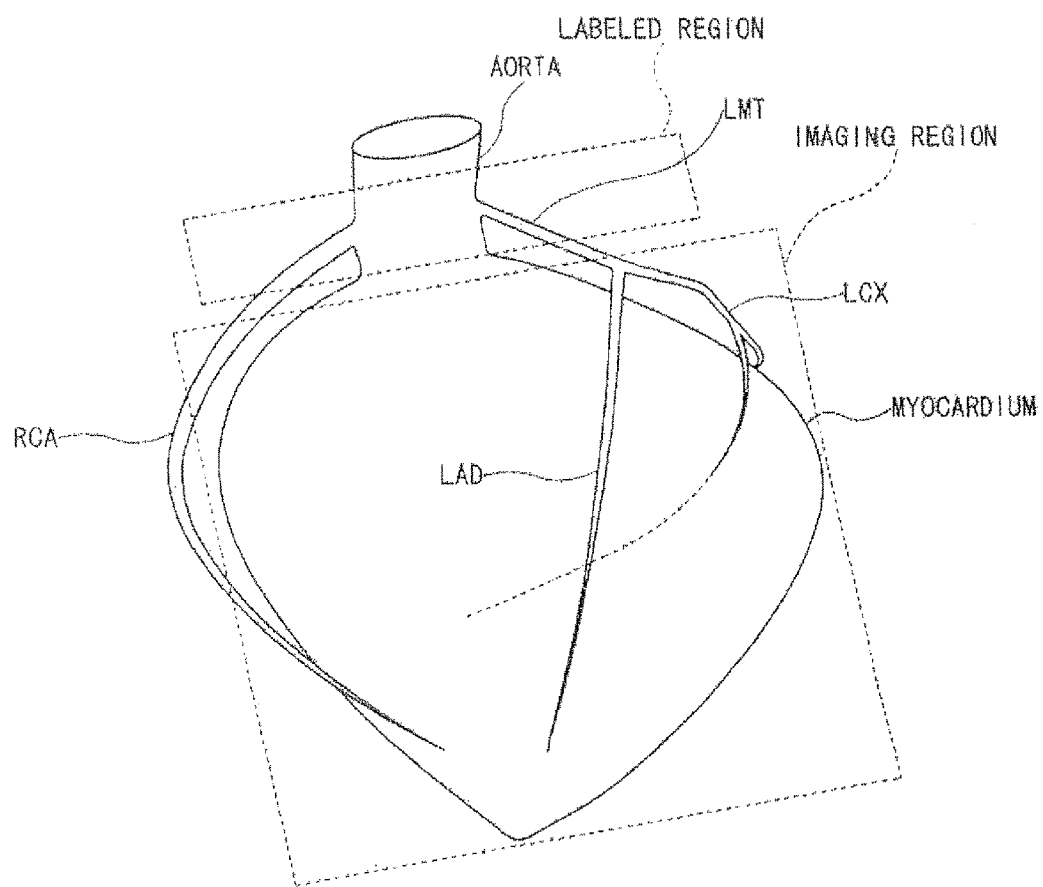
FIG. 6 is a diagram showing the first example of a labeling region (labeled region) set in the imaging condition setting unit shown in FIG. 3.

FIG. 6 shows the first example of the labeling region (i.e., labeled region) set in the imaging condition setting unit 40 shown in FIG. 3.

As shown in FIG. 6, the myocardium is provided with blood from the LMT, the RCA, the LCX and the LAD, each branching from the aorta. Then, as shown in FIG. 6, the slab including "the vent from the aorta to the LMT" and "the vent from the aorta to RCA" can be set as the labeling region. Moreover, by setting the imaging region to the myocardium part, imaging can be performed with emphasized signals of the blood reaching the myocardium via the LMT or RCA after BBTI.

Figure 7:
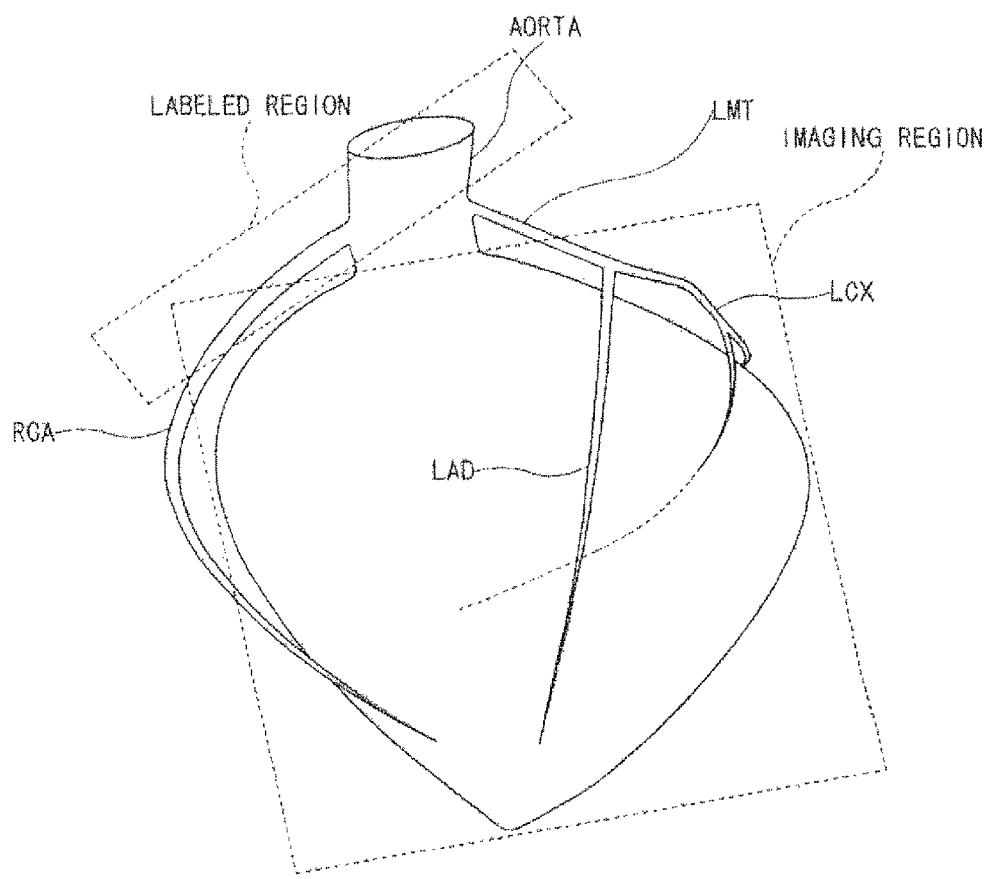
FIG. 7 is a diagram showing the second example of a labeling region (labeled region) set in the imaging condition setting unit 40 shown in FIG. 3.
Figure 8:
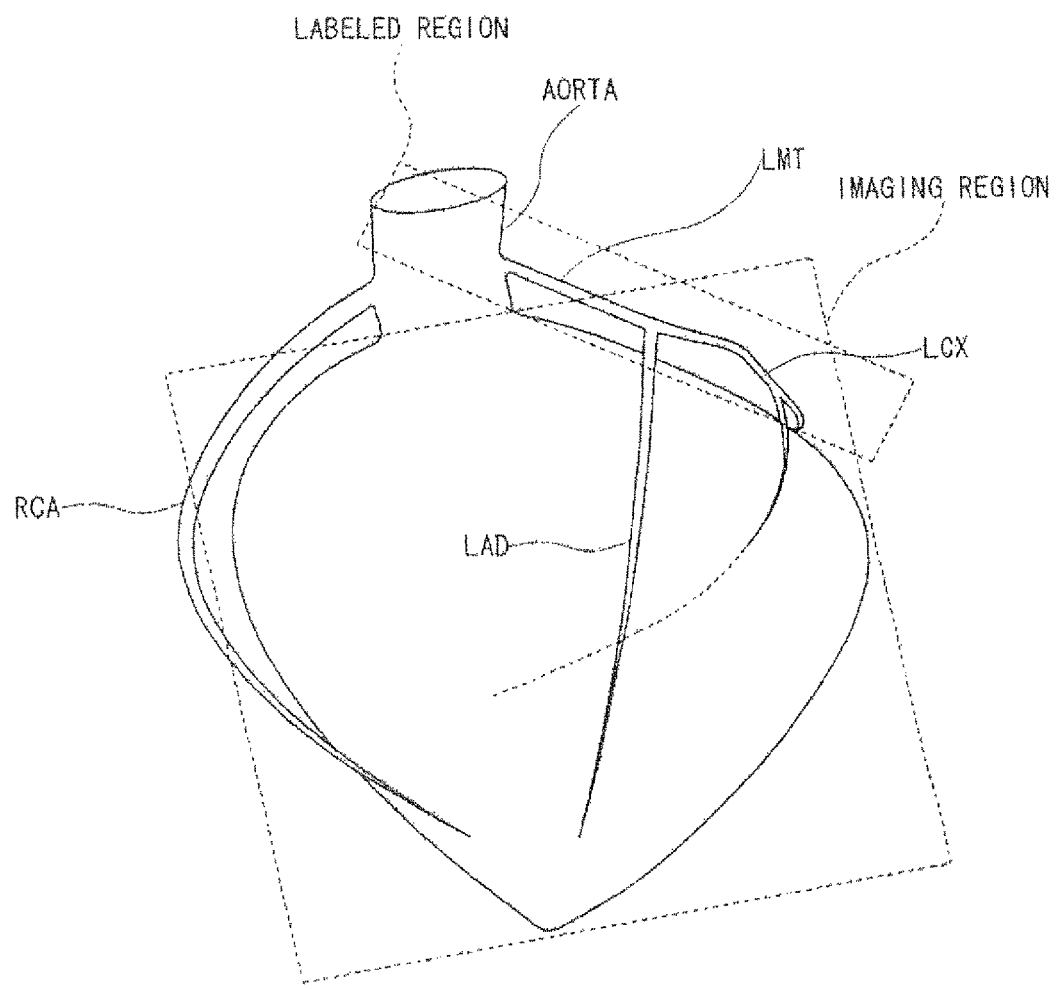
FIG. 8 is a diagram showing the third example of a labeling region (labeled region) set in the imaging condition setting unit 40 shown in FIG. 3.

FIG. 7 shows the second example of the labeling region (labeled region) set in the imaging condition setting unit 40 shown in FIG. 3 and FIG. 8 shows the third example of the labeling region set in the imaging condition setting unit 40.

As shown in FIG. 7, the labeling region including only the RCA can be set by adjusting the direction of slab selection and by setting the slab for partial excitation.

In the similar way, the labeling region can be set to the slab including only the LMT, as shown in FIG. 8, the range of blood provided from a labeled vessel in the myocardium can be specified by selectively labeling the specified vessel in the aforementioned manner. Also, the vessel providing blood to a specified region of the myocardium can be specified. Additionally, the labeling region can be set to the slab including only the LCX or LAD in a similar way.

Figure 9:
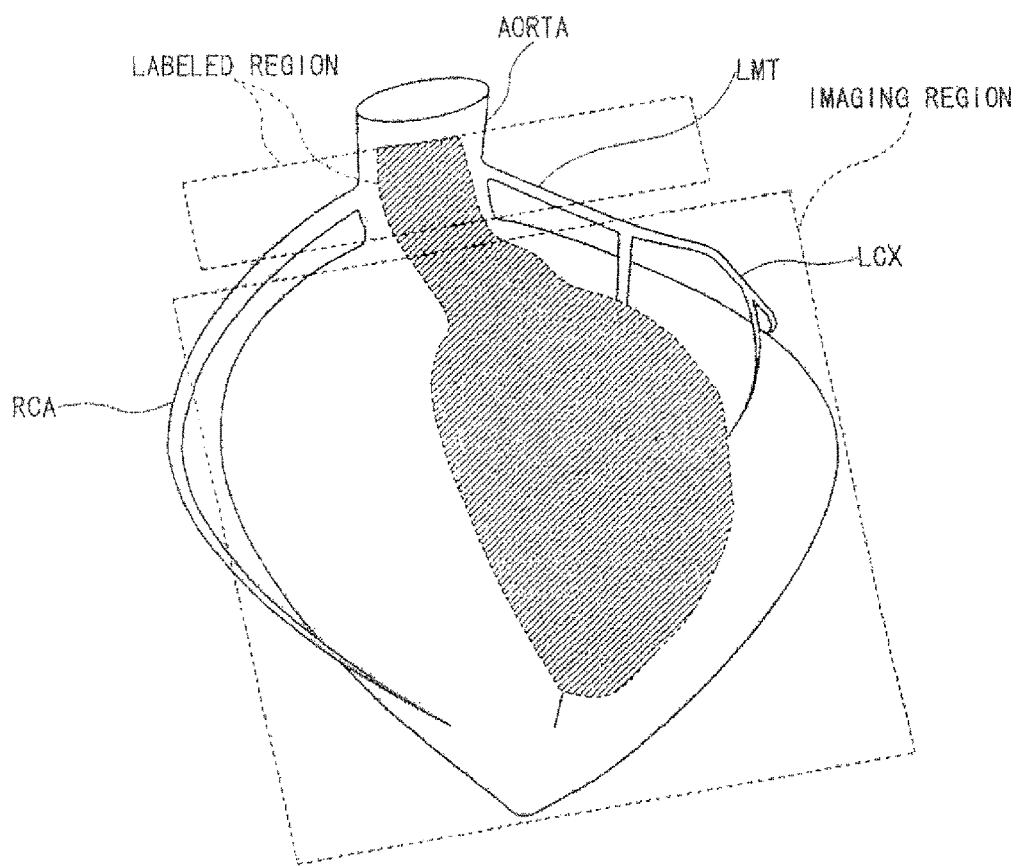
FIG. 9 is a diagram showing the fourth example of a labeling region (labeled region) set in the imaging condition setting unit 40 shown in FIG. 3.

FIG. 9 shows the fourth example of the labeling region (labeled region) set in the imaging condition setting unit 40 shown in FIG. 3.

As shown in FIG. 9, if the slab on the aorta as well as the slab inside the ventricle shown as shaded area are set as labeling regions, it is possible to label blood. Thereby, the volume of the labeled blood can be maintained, and the labeled blood can be provided inside the myocardium for a longer time. A slab inside the ventricle can be excited selectively by using "2D (two-dimensional) localized excitation" or "the combination of 2D localized excitation and 3D slab excitation".

Figure 10:
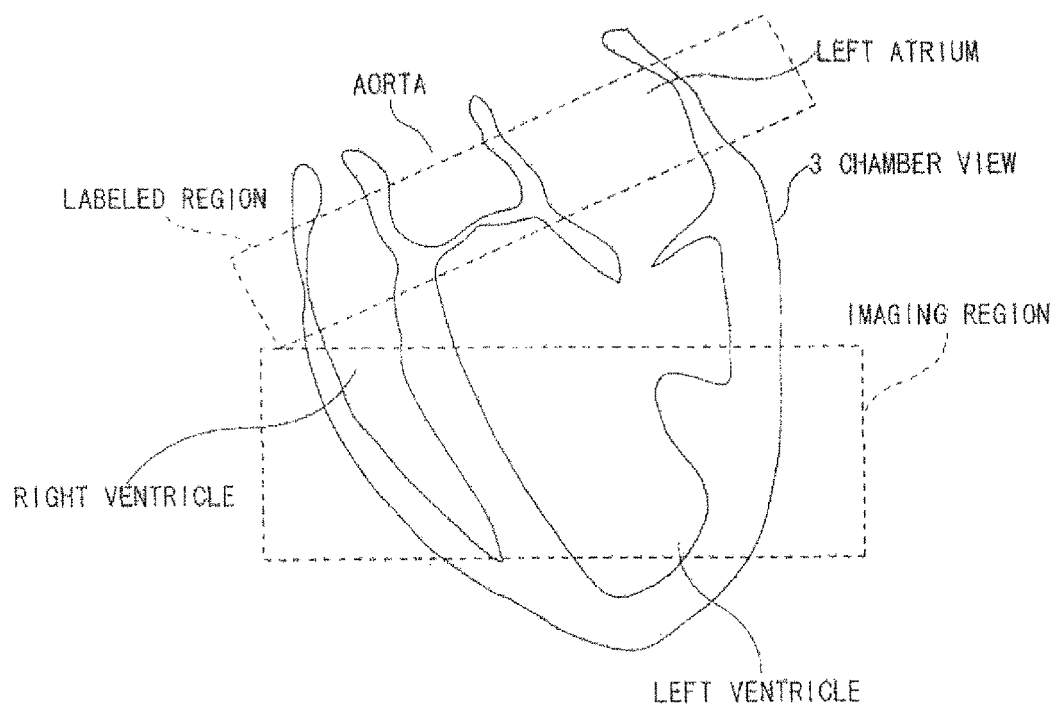
FIG. 10 is a diagram showing the fifth example of a labeling region (labeled region) set in the imaging condition setting unit 40 shown in FIG. 3.
Figure 11:
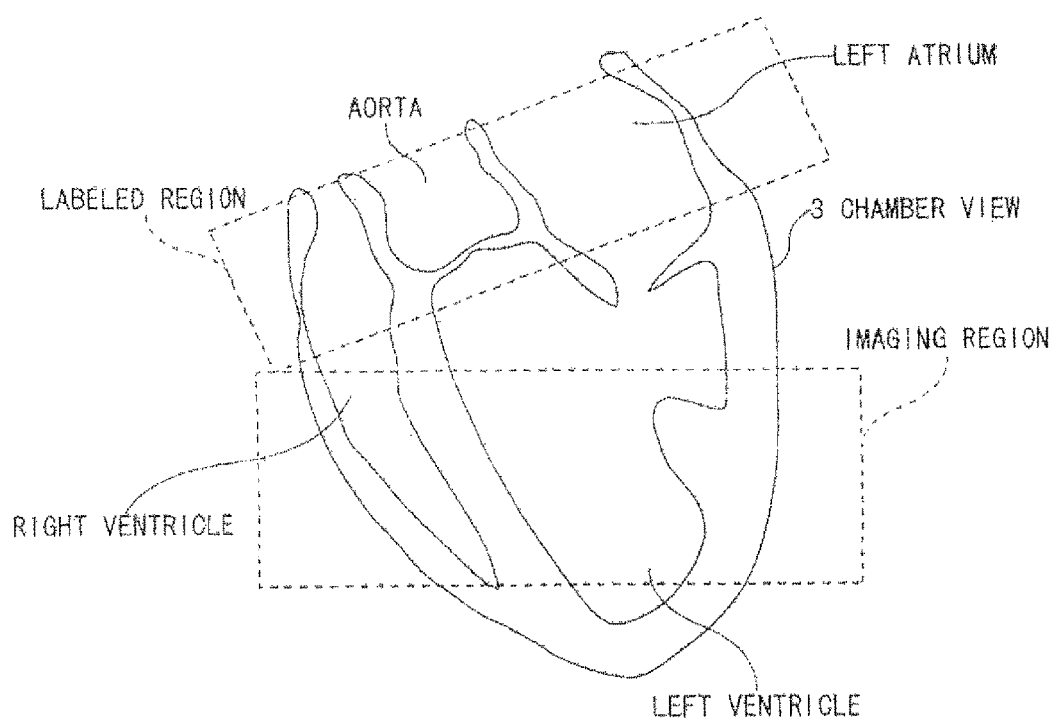
FIG. 11 is a diagram showing the sixth example of a labeling region (labeled region) set in the imaging condition setting unit 40 shown in FIG. 3.

FIG. 10 shows the fifth example of the labeling region (labeled region) set in the imaging condition setting unit 40 shown in FIG. 3, and FIG. 11 shows the sixth example of the labeling region (labeled region) set in the imaging condition setting unit 40 shown in FIG. 3.

As shown in FIG. 10, the labeling region can be set by using "a 3-chamber view image (In and Out Flow View) in the cross-section displaying 3 chambers of a right ventricle, a left ventricle and a left atrium" as a scout image (positioning image). In this case, the labeling region can be set easily and accurately to a slab including the vent of the coronary artery in the cardiac basal side.

Here, if the width of the labeling region is narrow, the reaching distance of the labeled blood becomes shorter according to the decreased amount of the labeled blood and consequently the labeled blood does not reach with enough quantity in some cases.

Then, as shown in FIG. 11, (the width of) the labeling region (labeled region) can be set wider but exclusive of the imaging region in the 3-chamber view image. In this case, it is possible to set a longer BBTI, because the reaching distance of the labeled blood becomes longer.

The 3-chamber view image can be acquired by using a known technology. Concretely speaking, the 3-chamber view image can be acquired, e.g., by repeating "acquisition of a scout image on a linear ROI (region of interest)" and "setting of a linear ROI in the acquired scout image". For example, a 2D SSFP sequence can be used for acquiring the 3-chamber view image.

Figure 12:
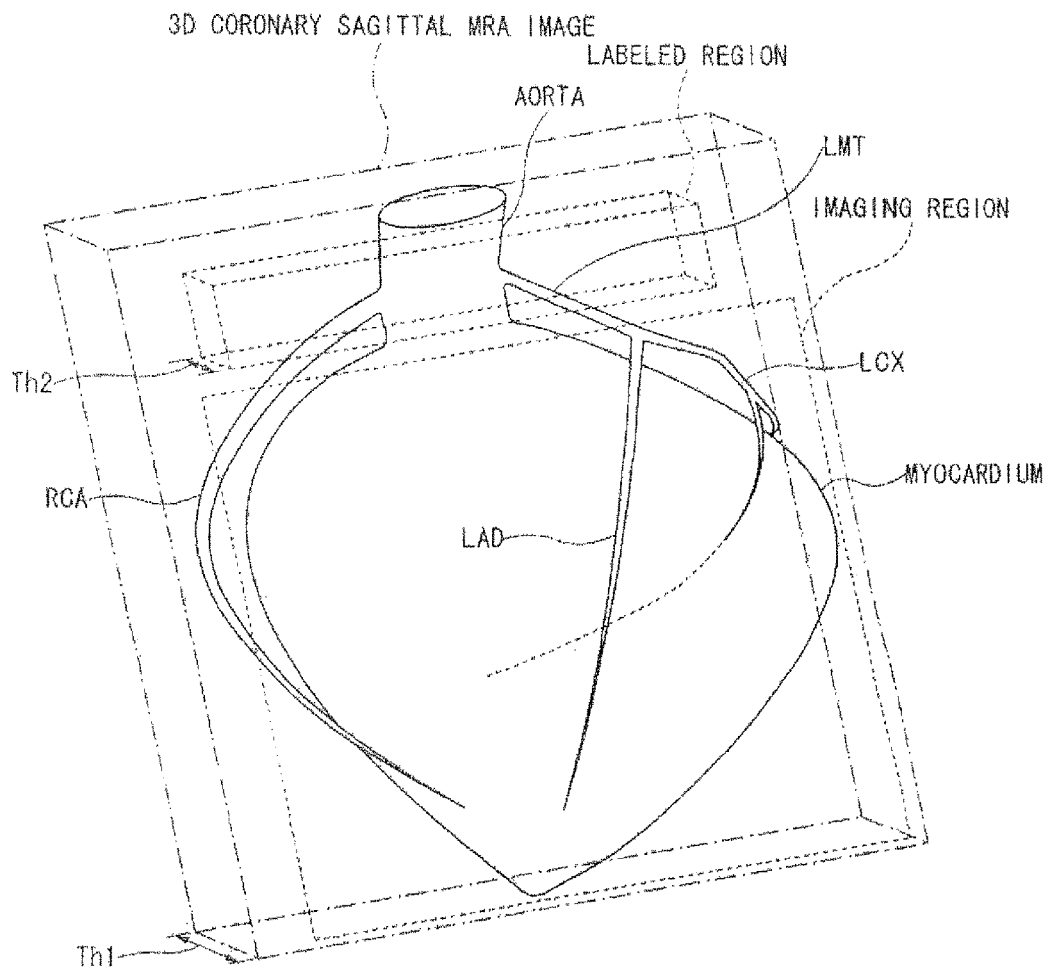
FIG. 12 is a diagram showing the seventh example of a labeling region (labeled region) set in the imaging condition setting unit 40 shown in FIG. 3.

FIG. 12 shows the seventh example of the labeling region (labeled region) set in the imaging condition setting unit 40 shown in FIG. 3. As shown in FIG. 12, the labeling region can be set with display of "a 3D-MRA image including the coronary artery in parallel with an object and a cardiac sagittal plane" as a scout image. Also in this case, the labeling region can be set easily and precisely to a slab inclusive of the vent of the coronary artery, because branching behavior of the coronary artery is visible.

3D-MRA image data of the coronary artery can be acquired in a shorter period, if the 3D-MRA image data are set as image data of thickness Th1 which is thin enough to be acquired during breath hold. On the contrary, a scout image of wider range for setting the labeling region can be acquired, if the 3D-MRA image data of the coronary artery are acquired under natural respiration with the aforementioned correction inhibiting the influence of motion caused by respiration.

As shown in FIG. 12, the labeling region can be set, e.g., as "a region having infinite thickness" or "a slab having finite thickness Th2 on the 3D-MRA image displayed sterically". Alternatively, the labeling region can be set as "a region having infinite thickness" or "a slab having finite thickness on projection image data such as MIP (maximum intensity projection) image data acquired from the 3D-MRA image data". Moreover, as another example, the labeling region can be set on 2D-MRA image data in an appropriate cross-section acquired from the 3D-MRA image data.

Although FIG. 4 shows an example of imaging by using a Flow-Out method of the time-SLIP method, imaging can be performed by using a Flow-In method and an On-Off Alternative difference method.

The Flow-Out method is a method of inhibiting signals of myocardium by applying a spatial non-selective 180° IR pulse as shown in FIG. 4, while acquiring imaging data at the same timing as blood labeled by the spatial selective 180° IR pulse in the labeling region near a coronary artery is perfused into the myocardium. Note that in the Flow-Out method, the spatial non-selective 180° IR pulse can be set OFF.

The Flow-In method is a method of applying only the spatial selective 180° IR pulse(s) to an imaging region including myocardium with the spatial non-selective 180°

IR pulse set OFF. In this method, imaging can be performed so that blood flowing into the imaging region after the application of the spatial selective 180° IR pulse is distinguished from other parts of excited state. This is because the blood flowing into the imaging region after the application of the spatial selective 180° IR pulse is not influenced by the spatial selective 180° IR pulse (is in an unexcited state).

The On-Off Alternative difference method is a method of generating difference image data between an On image and an Off image as blood flow image data. The On image is an image whose image data are acquired at the timing when blood labeled by a spatial selective 180° IR pulse in the labeling region near a coronary artery flows into myocardium, in a way similar to the Flow-Out method. The Off image is an image whose image data are acquired without applying the spatial selective 180° IR pulse (with other imaging conditions set the same as the On image). In the On-Off Alternative difference method, signals from labeled blood can be extracted selectively and blood flow image data can be generated by using the extracted blood signals.

Note that it is more desirable to perform data acquisition of On images and data acquisition of Off images alternately than to perform data acquisition of all the Off images after finishing data acquisition of all the On images needed for generating blood flow image data. This is because interval of imaging time between each On image and each Off image is shorter in the former, and influence of motion of an object (motion artifact) is smaller in the former.

Imaging conditions for acquiring blood flow image data corresponding to a plurality of BBTIs respectively are set in the imaging condition setting unit 40 by changing BBTI in the time-SLIP method. That is, a plurality of mutually different BBTIs is set as imaging conditions in the imaging condition setting unit 40.

Additionally, the delay time td1 and td2 of a pulse sequence based on an appropriate R wave are set in the imaging condition setting unit 40, so that data acquisition timing is in the same cardiac time phase or in closer cardiac time phase between different BBTIs, as mentioned above. Although the setting of these delay time td1 and td2 can be performed automatically in the imaging condition setting unit 40, it can be set manually by inputting necessary information to the imaging condition setting unit 40 through the input device 33.

Although the delay time td1 of a pulse sequence may be set to a time interval from the timing of an R wave to the application timing of the spatial non-selective 180° IR pulse as shown in FIGS. 4 and 5, the delay time td1 may be set by using another criterion of the pulse sequence. Moreover, a time condition influencing other data acquisition timing may be adjusted as a delay time of a pulse sequence instead of the delay time td1 from an R wave. For example, a time interval from the timing of an R wave to the application timing of spatial selective 180° IR pulse (td1+ΔT in FIG. 4) can be set as a delay time. In this case, an appropriate delay time can be determined automatically or manually according to BBTI.

For example, when the first BBTI is 1200 ms (millisecond) and the delay time (td1+ΔT) from the timing of R wave to the application timing of spatial selective 180° IR pulse is 400 ms, start timing of data acquisition is 1600 ms after the timing of the R wave. Thus, when the second BBTI is 1400 ms, the start timing of the data acquisition can be set in the same cardiac time phase by setting "the delay time (td1+ΔT) from the timing of the R wave to the application timing of the spatial selective 180° IR pulse" to 200 ms.

According to the above calculation method, imaging conditions of each sequence such as the delay time td1 can be calculated automatically so that the cardiac time phase of the start timing of the data acquisition accords through respective sequences having mutually different BBTIs. This automatic calculation may be performed according to (A) "values of time parameters such as BBTI and TI in the sequence whose BBTI value is selected as a reference value (criterion)" and (B) "a priority condition as to which time parameter such as ΔT is preferentially used to determine imaging conditions of other sequences (sequences whose BBTI values are not the reference value)". Thereby, values of each time parameter of sequences corresponding to other BBTI can be set automatically by setting only (A) "values of each time parameters in the sequence whose BBTI value is selected as criterion" and (B) the aforementioned priority condition. According to the above automatic setting method, the number of imaging conditions a user should set is required less, and this leads to improvement of operability of an MRI apparatus.

In the Flow-Out method and the On-Off Alternative difference method, BBTI corresponds to traveling time of labeled blood. Additionally, BBTI corresponds to traveling time of unexcited blood in the Flow-In method. That is, BBTI corresponds to traveling time of blood flowing into an imaging region. Thus, if imaging is performed with different BBTIs, a plurality of blood flow image data having mutually different reaching positions of blood respectively can be acquired. For example, BBTI is set to 600 ms, 800 ms, 1000 ms and 1200 ms.

Next, setting method of TI and BBTI will be explained.

The imaging parameter determining unit 40B has a function of setting TI and BBTIs. TI and BBTIs can be set individually and can be determined by a prescan respectively. Note that the "prescan" and "prep scan" discussed later mean operation from pulse application such as a slice selective pulse necessary for data acquisition to completion of generation of image data by using image reconstruction processing.

The prescan condition setting unit 40A has a function of setting imaging conditions of a TI-prep scan which is a prescan for determining TI and has a function of setting imaging conditions of BBTI-prep scan which is a prescan for determining BBTIs.

FIG. 13 is a chart explaining determination method of TI and BBTIs set as imaging conditions in the imaging condition setting unit 40 shown in FIG. 3.

In FIG. 13, the abscissa axis indicates elapsing time t. As shown in FIG. 13(A), imaging conditions of the TI-prep scan performing data acquisition plural times with mutually different TI (TI1, TI2, TI3, . . . , TIn) are set (note that "n" represents the number of TIs). An arbitrary sequence, which can be used for an imaging sequence such as the FASE sequence, can be used for the data acquisition sequence of the TI-prep scan. Note that it is desirable to use the same sequence as the imaging sequence for the data acquisition of the TI-prep scan. Additionally, it is desirable to use a 2D sequence for the data acquisition of the TI-prep scan in order to shorten time needed for the data acquisition.

As shown in FIG. 13(B), blood flow cross-sectional images are generated by performing the TI-prep scan, and thereby blood flow cross-sectional images I(TI1), I(TI2), I(TI3), . . . , I(TIn) are acquired. Then, an appropriate TI (TIopt) can be determined by selecting the blood flow cross-sectional image (corresponding to TIopt) with the best contrast out of the plurality of blood flow cross-sectional images I(TI1), I(TI2), I(TI3), . . . , I(TIn). That is, information on determination of TI value can be inputted into the imaging parameter determining unit 40B through the input device 33 as selection information on blood flow cross-sectional images.

Note that the imaging parameter determining unit 40B may be provided with a function of automatically selecting the blood flow cross-sectional image with good contrast by using data processing such as threshold processing.

In the similar way, imaging conditions of a BBTI-prep scan performing data acquisition plural times with mutually different BBTIs (BBTI1, BBTI2, BBTI3, . . . , BBTIm) are set as shown in FIG. 13(C) (note that "m" represents the number of BBTIs). An arbitrary sequence, which can be used for an imaging sequence such as the FASE sequence, can be used for the data acquisition sequence of the BBTI-prep scan. Note that it is desirable to use the same sequence as the imaging sequence for the data acquisition of the BBTI-prep scan. Additionally, it is desirable to use a 2D sequence for the data acquisition of the BBTI-prep scan in order to shorten time needed for the data acquisition.

As shown in FIG. 13(D), blood flow cross-sectional images are generated by performing the BBTI-prep scan, and thereby blood flow cross-sectional images I(BBTI1), I(BBTI2), I(BBTI3), . . . , I(BBTIm) are acquired. Then, out of the plurality of blood flow cross-sectional images I(BBTI1), I(BBTI2), I(BBTI3), . . . , I(BBTIm), a range of blood flow cross-sectional images I(BBTIst), . . . , I(BBTIend), in which traveling distance of blood flowing into the imaging region is in appropriate range, are selected. By this selection, an appropriate range of BBTIs (from BBTIst to BBTIend) are determined. That is, "plural BBTI values as selection information on blood flow cross-sectional images" or "determination information on default, final value and changing amount of BBTI" can be inputted into the imaging parameter determining unit 40B through the input device 33.

For example, by performing 2-dimensional imaging with plural BBTIs ranging from 100 ms to 2000 ms with increment of 100 ms, BBTIs ranging from 600 ms to 1200 ms with increment of 200 ms may be determined for imaging. By this way, changing amount of BBTI values for imaging may be changed from that of the BBTI-prep scan.

It is desirable to set imaging cross-sections of the BBTI-prep scan to "an arbitrary plane inclusive of the cardiac long axis" or "a plurality of long axial planes rotated around the cardiac long axis". This is so that the myocardial cross-sectional position in the cardiac long axial direction, where the blood labeled according to BBTI reaches, is visible on the BBTI-prep image.

That is, in terms of determining appropriate BBTI and its variation range, it is desirable to set the BBTI-prep images to the same images as scout images for setting the labeling region or 2D images in parallel with these scout images.

Then, 3D imaging can be performed using appropriate TI (TIopt) and a plurality of BBTIs (BBTIst, . . . , BBTIend) as imaging conditions as shown in FIG. 13(E).

An appropriate TI value and a plurality of appropriate BBTIs are different according to conditions such as age, sexuality, body height and body weight of an object, stage of progression in a lesion area and an imaging region. Then, a database of an appropriate TI value and a plurality of appropriate BBTIs can be empirically compiled per each of the those conditions. That is, a table data (table-type database) indicative of an appropriate TI value and a plurality of appropriate BBTIs per each of the conditions of an object can be stored in the imaging parameter storing unit 40C.

In this case, when information on the conditions of an object is inputted to the imaging parameter determining unit 40B by operating input device 33, the imaging parameter determining unit 40B can refer to the table data on the imaging parameter storing unit 40C and can obtain an appropriate TI value and/or a plurality of appropriate BBTIs corresponding to the inputted conditions. In this manner, an appropriate TI value and/or a plurality of appropriate BBTIs corresponding to conditions of an object can be determined without performing the TI-prep scan and/or the BBTI-prep scan.

Next, other functions of the computer 32 will be explained.

The sequence controller control unit 41 has a function of acquiring imaging conditions including pulse sequences from the imaging condition setting unit 40 based on command information on start of imaging, and performing drive control of the sequence controller 31 by inputting the acquired imaging conditions to the sequence controller 31. Additionally, the sequence controller control unit 41 has a function of receiving raw data from the sequence controller 31 and arranging the raw data in k-space formed in the k-space database 42.

The blood flow image generating unit 43 has a function of obtaining k-space data from the k-space database 42, and generating a plurality of blood flow image data corresponding to mutually different BBTIs by performing image reconstruction processing including FT (Fourier transformation) and necessary image processing. Additionally, the blood flow image generating unit 43 has a function of writing the generated blood flow image data onto the image database 44.

For example, in the case of the On-Off Alternative difference method, the blood flow image generating unit 43 performs image processing of difference data between "On image data acquired by performing labeling with the spatial selective 180° IR pulse" and "Off image data acquired without performing labeling".

Moreover, in the case of correcting respiratory motion by using the RMC method, the blood flow image generating unit 43 performs phase correction of the k-space data with shift amount corresponding to amount of respiratory motion and positional correction of blood flow image data so as to remove the influence of respiratory motion. The amount of respiratory motion can be determined, for example, as amount of variation from a reference value of real space data obtained by performing FT on the k-space data such as the MPP acquired for detecting respiratory level.

Moreover, the blood flow image generating unit 43 has a function of performing correction processing. In this correction processing, signal components of telae is removed from "image data obtained by performing image reconstruction processing on the k-space data" and only the blood flow signal components are extracted as the blood flow image data.

FIG. 14 is an explanatory chart showing the generation processing of the blood flow image data performed by the blood flow image generating unit 43. In the generation processing, signal components except blood is removed from image data.

Figure 14A:
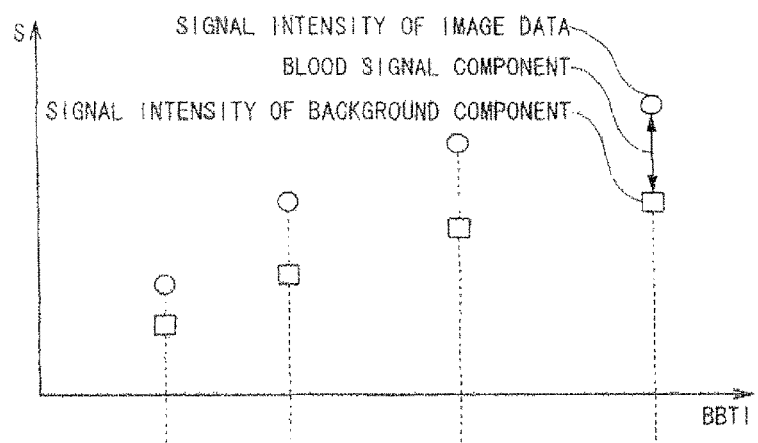
FIGS. 14A-B are diagrams for explaining the process of generating blood flow image data executed in the blood flow image generating unit by eliminating signal component except blood from image data.
Figure 14B:
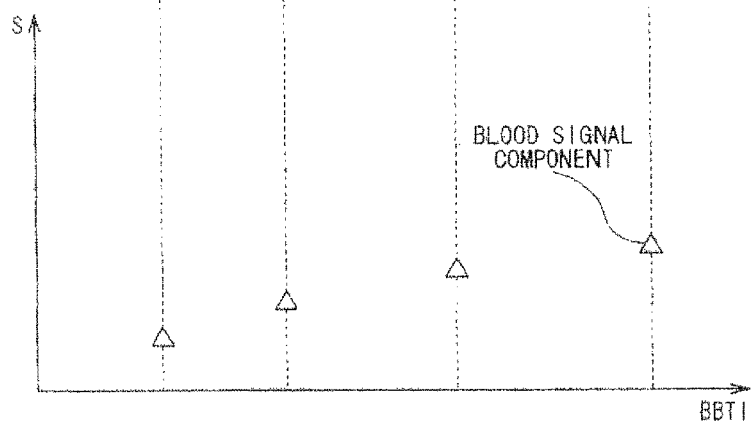

In each of FIGS. 14(A) and 14(B), the abscissa axis indicates time length of BBTI (second) and the vertical axis indicates signal intensity S. In FIG. 14(A), signal values of image data are plotted per BBTI. As shown in FIG. 14(A), the longer BBTI is, the stronger the signal intensity S of the image data becomes. This is because the longitudinal magnetization components of telae (tissues) and unlabeled blood recover according to the length of BBTI. That is, the longer BBTI is, the more signal component from the background is superimposed and this changes the base line of the blood signal. Thus, in order to determine signal intensity of the blood flow image data more accurately, it is desirable to perform base line correction in which signal components from the labeled blood are extracted by removing signal components of the background from the image data.

Therefore, the blood flow image generating unit 43 has a function of generating the blood flow image data as shown in FIG. 14(B) by performing the aforementioned base line correction on image data. The base line correction can be performed by subtracting the background component except labeled blood from the image data. Note that the base line correction may be performed on the k-space data before the image reconstruction processing instead of the image data alternatively. Signal values of the background components can be determined by imaging or by performing simulation of a T1 recovery curve of longitudinal magnetization component Mz.

As the imaging for determining the signal value of the background component, for example, there is a method of applying a spatial non-selective 180° IR pulse to invert the longitudinal magnetization component Mz of the background part without applying a spatial selective 180° IR pulse for labeling blood. Alternatively, the signal value of the background component can be acquired by imaging in which the labeling region is set as a region whose labeled blood does not flow into the imaging region at the timing of data acquisition. Additionally, if the signal value of the background component is acquired by imaging for only a part of the imaging region that needs the base line correction, imaging time and data processing amount are decreased.

The blood flow information generating unit 45 has a function of (A) obtaining a plurality of blood flow image data corresponding to mutually different BBTIs respectively from the image database 44, (B) performing cardiac function analysis based on the plurality of blood flow image data, (C) generating blood flow information indicating cardiac function in myocardium in an arbitrary description method as the result of the cardiac function analysis, and (D) displaying the blood flow information on the display device 34.

As an example of display of the blood flow information, there is a method of performing parallel display of the plurality of blood flow images corresponding to mutually different BBTIs respectively. Then, the longer BBTI a blood flow image corresponds to, the longer distance the blood flow image indicates as traveling distance of the emphasized blood flowing into the imaging region. This is because BBTI corresponds to supply time of blood to the imaging region. That is, a plurality of blood flow images indicating respectively different traveling distances of blood can be displayed corresponding to each BBTI.

Moreover, blood flow image data having a time axis can be generated as the blood flow information like cine image data for consecutively displaying blood flow images on an image to image basis in the order of BBTI values. In this case, the blood flow images can be displayed so that the behavior of blood flow gradually flowing inside the myocardium is shown.

Additionally, a profile of the blood flow image data per BBTI at an arbitrary myocardial cross-sectional position can be generated as the blood flow information.

Figure 15A:
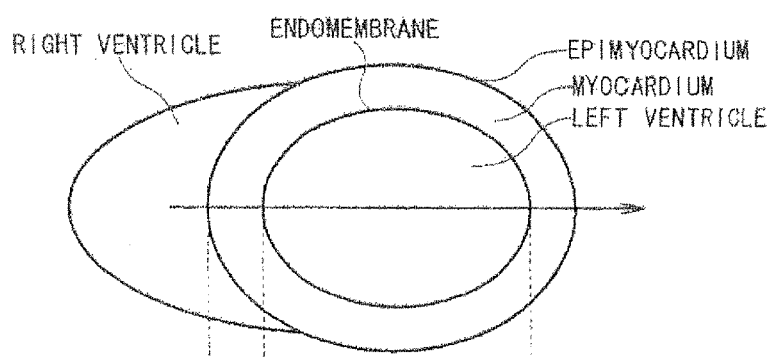
FIGS. 15A-B are diagrams showing an example of a profile of blood flow image data generated by the blood flow information generating unit 45 shown in FIG. 3.

FIG. 15 is a diagram showing an example of a profile of the blood flow image data generated by the blood flow information generating unit in FIG. 3. FIG. 15(A) shows a cross-sectional image including the myocardial short axis.

Figure 15B:
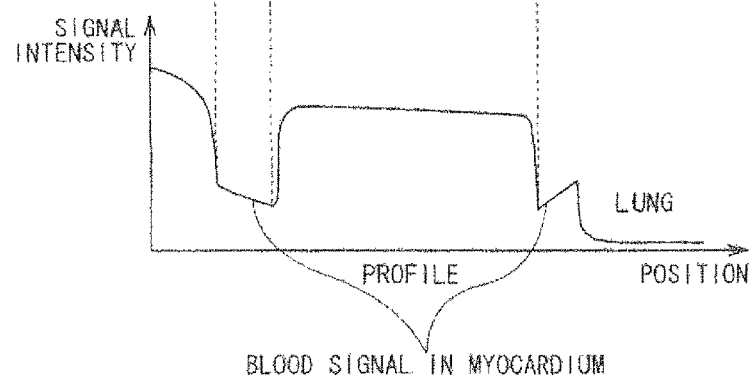
Figure 16A:
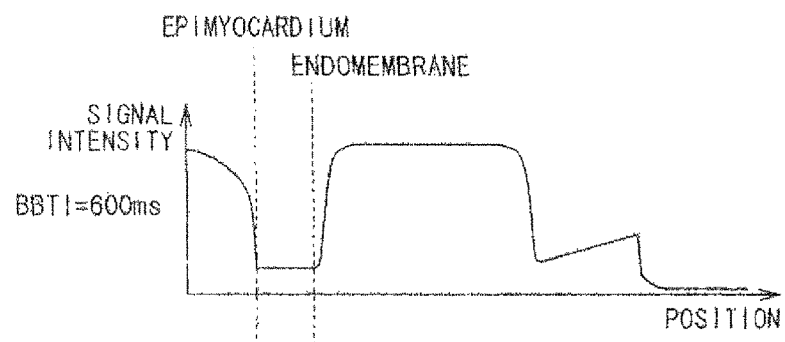
FIGS. 16A-D are diagrams showing an example of a set of profiles of blood flow image data corresponding to a plurality of different BBTIs generated by the blood flow information generating unit 45 shown in FIG. 3.
Figure 16B:
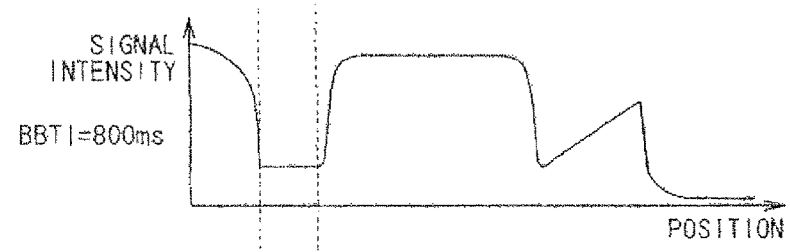
Figure 16C:
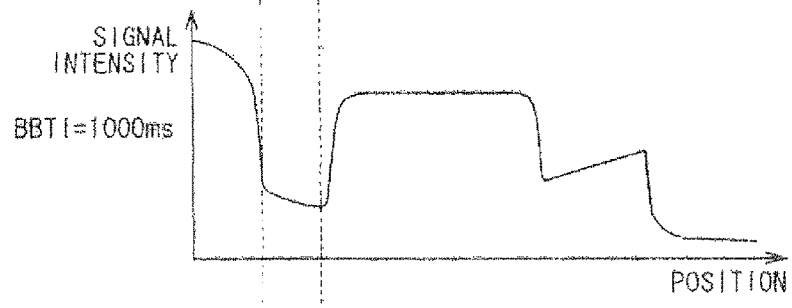
Figure 16D:
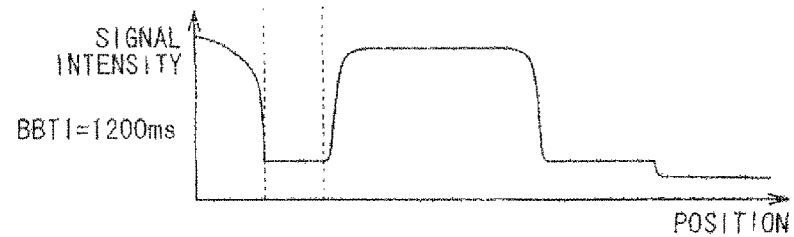

FIG. 15(B) shows the profile of the blood flow image data on a linear ROI (region of interest) set on the cross-sectional image including the myocardial short axis shown in FIG. 15(A). That is, the abscissa axis in FIG. 15(B) shows cross-sectional positions on the myocardial short axis and the vertical axis in FIG. 15(B) shows signal intensity of the blood flow image data.

As shown in FIG. 15(B), the myocardium is covered with its endocardium (endomembrane) and epimyocardium (epicardium), and the left ventricle is formed inside the myocardium. Additionally, the left ventricle is adjacent to the right ventricle. By generating a profile in the direction of the short axis in such myocardial cross-section, the data shown in FIG. 15(B) are obtained. Because blood flow amount inside the myocardium is small compared with the inside of the left and right ventricles, the blood signal intensity inside the myocardium is relatively small as shown in FIG. 15(B). A profile like FIG. 15(B) can be made per BBTI.

FIG. 16 is a diagram showing an example of a set of profiles of the blood flow image data corresponding to a plurality of different BBTIs. Note that these profiles are made by the blood flow information generating unit in FIG. 3. In FIG. 16, each vertical axis shows blood signal intensity and each abscissa axis shows positions in the direction of the myocardial short axis.

For example, as shown in FIGS. 16(A), 16(B), 16(C) and 16(D), profiles of the respective blood flow image data in the case of changing BBTI such as 600 ms, 800 ms, 1000 ms and 1200 ms can be made. Then, by displaying the respective profiles of the blood flow image data corresponding to a plurality of different BBTIs for an arbitrary myocardial cross-section in parallel, these profiles can be compared with each other.

Blood, which has flowed into the imaging region, flows into the inside of the myocardium from the epimyocardium and flows into the inside of the left ventricle from the endocardium. Thus, after the signal intensity near the epimyocardium has gradually increased according to the extension of the BBTI, the signal intensity near the endocardium increases due to the movement of blood toward the endocardium side as shown in FIGS. 16(A), 16(B), 16(C) and 16(D). By this way, the traveling behavior of the blood in the myocardium according to change in BBTI can be observed as time change of signal intensity in the myocardium. Additionally, distribution of blood signal can be analyzed.

These profiles of the blood flow image data can be made and displayed 3-dimensionally, instead of being made as an arbitrary cross-section. In other words, a profile comprising 3 parameters, which are respective values in the 2 directions crossing on a myocardial cross-section (e.g., x coordinate value and y coordinate value) and signal value S, can be displayed as a oblique perspective figure in torus-shape (doughnut shape). Thereby a part with relatively low signal intensity can be easily found out.

Additionally, by performing sign inversion processing on the blood flow image data, highlight display can be performed in the way the lower signal intensity a part has, the higher brightness the part is displayed with. Then, even if the low signal intensity part such as an infarction part is localized, it can be easily discovered. Moreover, if the profile is displayed 3-dimensionally, a low signal intensity part can be observed as a peak.

Additionally, when the blood flow image generating unit 43 does not perform the aforementioned base line correction, it means that the background signal component is superimposed on the obtained profile. Then, the obtained profile can be displayed with different colors and a display method so that the respective signal components of the background and the labeled inflowing blood are distinguishable from each other.

Moreover, by calculating signal difference between a plurality of blood flow image data corresponding to different BBTIs respectively as the blood flow information, a lesion area such as an infarction area and an ischemia area in the myocardium can be specified based on the calculated signal difference.

Figure 17:
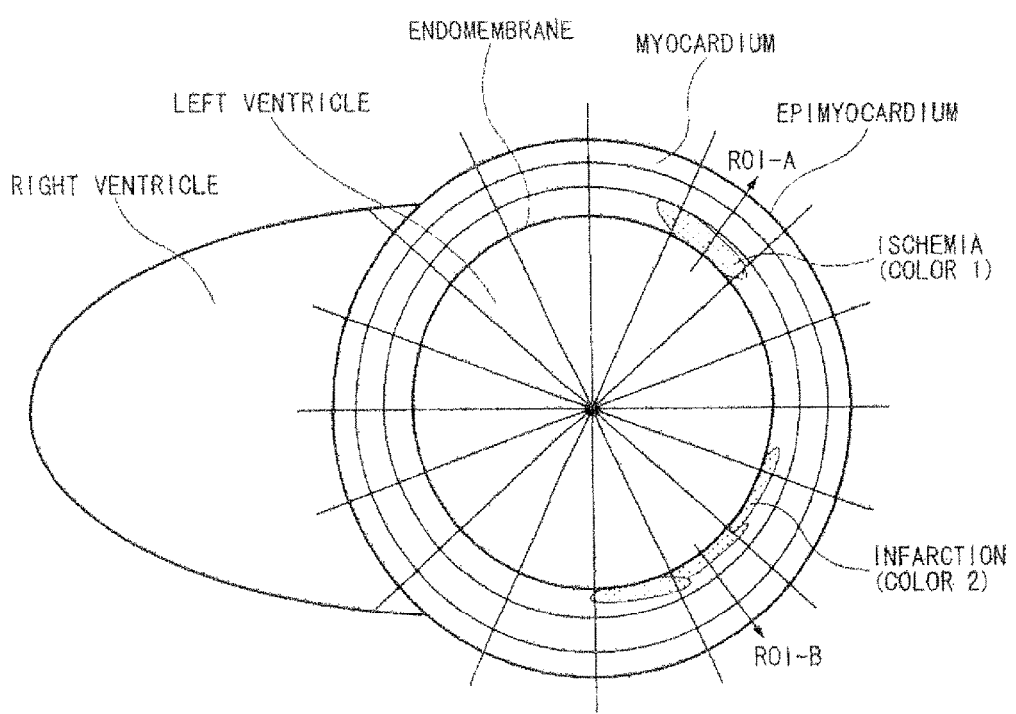
FIG. 17 is a diagram showing an example of distinguishably displayed lesion areas of myocardium identified by the blood flow information generating unit 45 shown in FIG. 3 based on signal differences between blood flow image data corresponding to different black blood inversion times (BBTIs)

FIG. 17 is a diagram showing an example of distinguishably displayed lesion areas of the myocardium identified by the blood flow information generating unit in FIG. 3 based on signal difference between blood flow image data corresponding to different BBTIs. FIG. 17 is a blood flow information image per segment displaying signal (signal intensity) difference between the blood flow image data corresponding to different BBTIs by dividing a short axial cross-section of the myocardium into a plurality of segments. That is, luminance display of the signal difference between the blood flow image data corresponding to different BBTIs is possible with high resolution as shown in FIG. 17, because the blood flow image data are acquired without using a contrast medium. Color display per segment with at least one of chromatic colors according to signal values is possible with regard to the signal difference.

In this case, the signal difference between 3-dimensional blood flow image data can be calculated on a pixel to pixel basis. Thereby, the blood flow information can be acquired with higher precision. In the case of calculating the difference values per pixel, each representative value such as an average value in each segment may be displayed.

Note that the signal differences between the blood flow image data may be displayed as bull's-eye display in which data of a plurality of mutually different myocardial cross-sections are displayed as one concentric image. Additionally, signal values of the blood flow image data can be displayed per segment.

For example, the delta (difference) between reference data and the blood flow image data corresponding to each BBTI can be calculated. In this case, the reference data are the data acquired without applying a spatial selective 180° IR pulse (i.e., acquired with BBTI set to zero). Then, the signal difference value according to traveling distance of blood at each data acquisition time can be obtained.

The signal difference value in a normal area is equal to or more than a constant value, because the amount of supplied blood is sufficient there. However, the signal difference value in an infarction area where blood is not supplied is zero, because blood signal does not change there. Additionally, the signal difference value in an ischemia area, where the amount of supplied blood is small, is low. This is because variation of blood signal is small there.

Thus, range of an infarction area can be detected by judging whether or not the signal difference value can be regarded as zero at each position and by specifying the region where the signal difference value can be regarded as zero. Additionally, range of an ischemia area can be detected by judging whether or not the signal difference value can be regarded as equal to or less than a threshold value corresponding to an ischemia part at each position and by specifying the region where the signal difference value can be regarded as equal to or less than the threshold value. A lesion area such as an infarction area and an ischemia area can be distinguishably (identifiably) displayed by using, e.g., different patterns as shown in "the color 1 part" and "the color 2 part" in FIG. 17. Although FIG. 17 is drawn in grayscale for reasons of expediency, "the color 1 part" and "the color 2 part" in FIG. 17 may be colored with different chromatic colors respectively so that they are distinguishably displayed as lesion areas.

Figure 18:
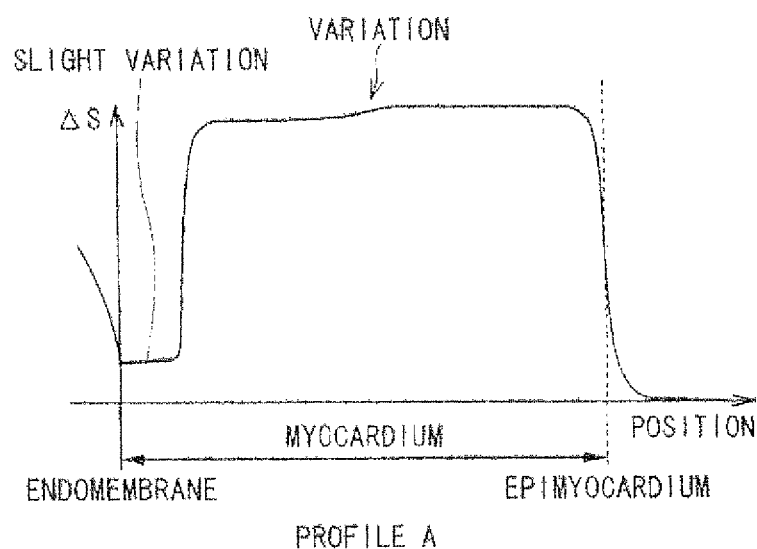
FIG. 18 is a diagram showing a signal difference in the line ROI-A crossing the ischemic area shown in FIG. 17.
Figure 19:
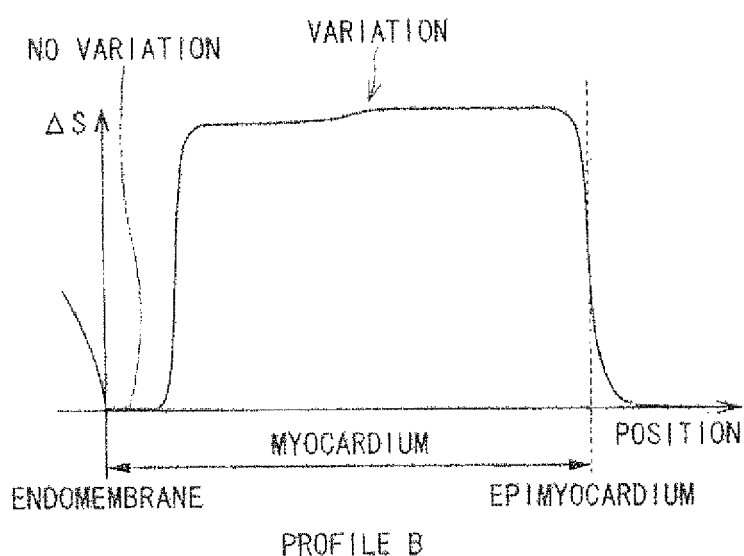
FIG. 19 is a diagram showing signal difference in the line ROI-B crossing the infarction area shown in FIG. 17.

FIG. 18 is a diagram showing the signal difference in the line ROI-A crossing the ischemia area shown in FIG. 17. FIG. 19 is a diagram showing the signal difference in the line ROI-B crossing the infarction area shown in FIG. 17.

In FIG. 18 and FIG. 19, each vertical axis indicates signal difference values ΔS between the blood flow image data corresponding to different BBTIs and each abscissa axis indicates positions on the linear ROI. As shown in FIG. 18, the signal difference value ΔS in the ischemia area (shown as "SLIGHT VARIATION") is small in the profile of the signal difference value on the linear ROI A in FIG. 17 crossing the ischemia area. Additionally, as shown in FIG. 19, the signal difference value ΔS in the infarction area (shown as "NO VARIATION") is zero in the profile of the signal difference value on the linear ROI B in FIG. 17 crossing the infarction area. Moreover, these curves of the signal difference values can be displayed as the blood flow information.

Figure 20:
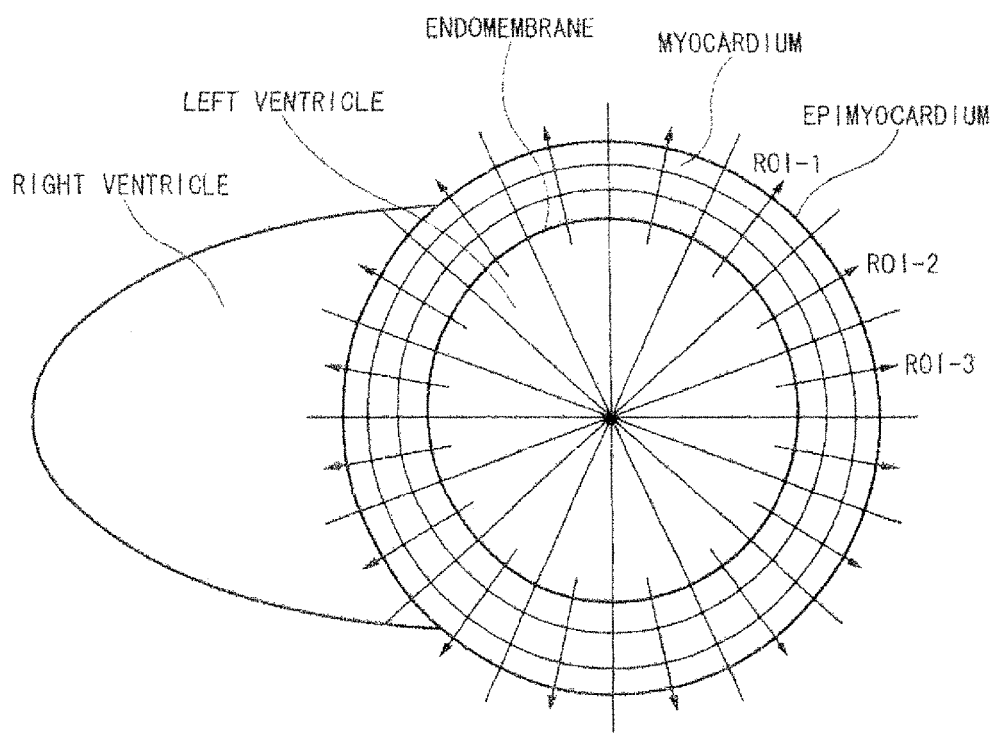
FIG. 20 is an example showing how the blood flow information generating unit 45 shown in FIG. 3 enables users to select display of each signal difference value between blood flow image data corresponding to different BBTIs in a plurality of line ROIs on a cross-section of myocardium.

FIG. 20 is an example showing how the blood flow information generating unit in FIG. 3 enables users to select the display of each signal difference value between the blood flow image data corresponding to different BBTIs in a plurality of linear ROIs on a cross-section of the myocardium.

FIG. 20 is a blood flow information image per segment displaying signal difference between the blood flow image data corresponding to different BBTIs by dividing a short axial cross-section of the myocardium into plural segments. As shown in FIG. 20, a plurality of linear ROIs (ROI-1, ROI-2, ROI-3, . . . ) can be selectively set on a blood flow information image. Then, if an arbitrary linear ROI is selected through the input device 33 by operation of, e.g., a mouse, the curve of the signal difference value ΔS on the selected linear ROI is displayed like FIGS. 18 and 19.

Note that a plurality of linear ROIs may be displayed as bulls-eye display. Additionally, the computer 32 may be configured to display a profile of signal values on the selected linear ROI by displaying signal values of the blood flow image data per segment, when an arbitrary linear ROI is selected out of a plurality of linear ROIs. Moreover, 3-dimensional display, sign inversion display, and distinguishable display of background component are possible with regard to a profile of the signal difference value ΔS in a way similar to the profile of signal intensity.

In addition, when the signal difference between the blood flow image data corresponding to different BBTIs is calculated, it is important that each of the blood flow image data for the calculation target indicates "the position of the myocardial cross-section" corresponding to the positions of the other blood flow image data. Then, as mentioned above, it is desirable to perform the positional correction of the blood flow image data so that (A) the cardiac time phase at the data acquisition timing accords with each other through the blood flow image data which are the calculation target of the difference value and (B) each position of the myocardial cross-section on the blood flow image data accords with each other. This is because the blood flow information can be acquired more precisely in that manner. The positional correction of the blood flow image data can be performed in the blood flow information generating unit 45.

Figure 21:
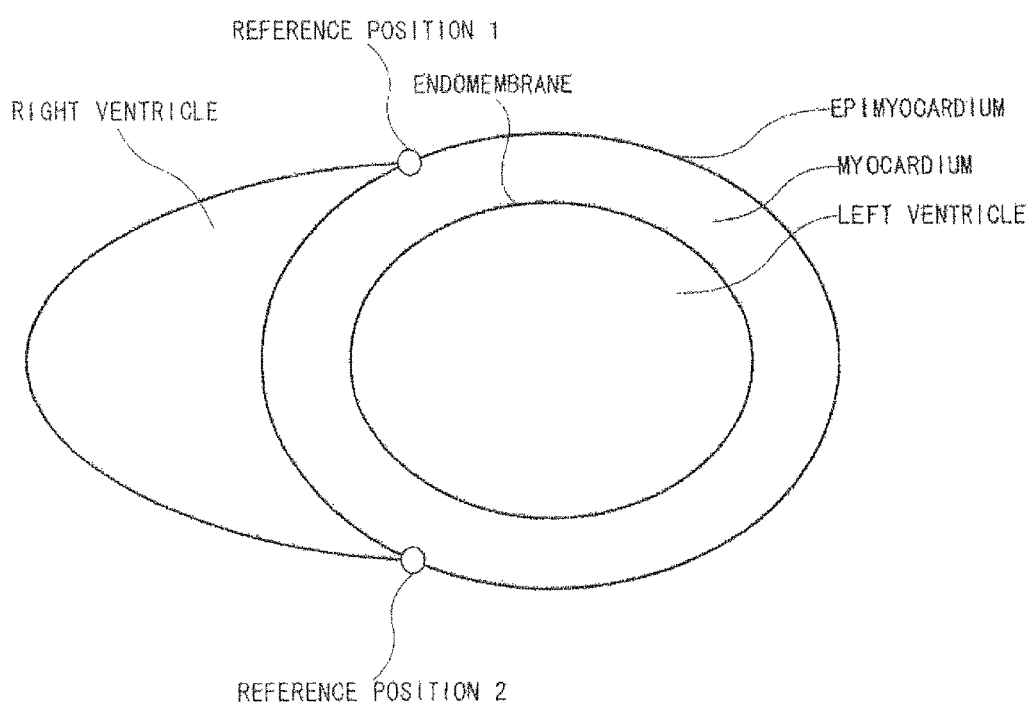
FIG. 21 is a diagram showing reference positions for the blood flow information generating unit 45 shown in FIG. 3 to perform positional correction between blood flow image data.

FIG. 21 is a diagram showing reference positions for the blood flow information generating unit 45 in FIG. 3 to perform the positional correction between the blood flow image data.

As shown in FIG. 21, the myocardium is covered with the endocardium (endomembrane) and the epimyocardium, and the left ventricle is formed inside the myocardium. Additionally, the left ventricle is adjacent to the right ventricle. On such a myocardial short axial cross-sectional image, the blood flow information such as the signal difference value can be acquired more accurately by setting one or plural reference position(s) at the border part between the left and right ventricles and by performing the positional correction such as parallel shift or rotational locomotion of the respective blood flow image data in the following manner. That is, the positional correction should be performed so that the reference positions more accord with each other through the blood flow image data corresponding to different BBTIs. Note that although the positional correction can be performed more easily in the case of setting 2 reference positions as shown in FIG. 21, the positional correction can be performed in the case of setting only one reference position.

(Operation and Action)

Next, the operation and action of the magnetic resonance apparatus 20 will be explained.

Figure 22:
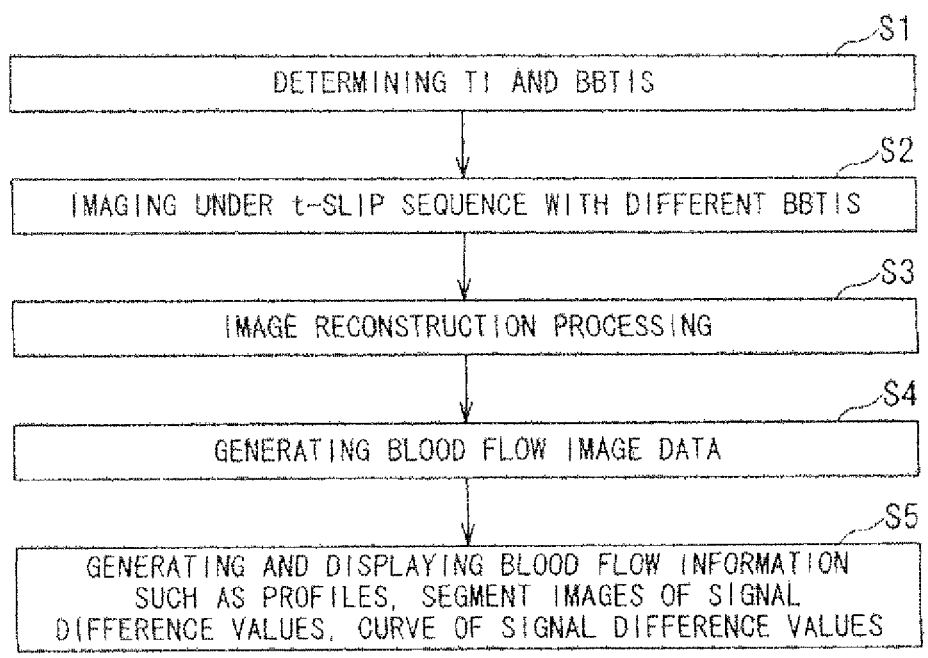
FIG. 22 is a flowchart showing a procedure for acquiring blood flow information on cross-sections of myocardium of an object P and displaying their images by performing a non-contrast MRA imaging with the magnetic resonance imaging apparatus 20 shown in FIG. 2.

FIG. 22 is a flowchart showing a procedure for acquiring the blood flow information on cross-sections of the myocardium of the object P and displaying their images by performing a non-contrast MRA imaging with the magnetic resonance imaging apparatus 20 shown in FIG. 2. Hereinafter, the case of performing imaging operation under the Flow-Out method of the time-SLIP method will be explained as an example.

First, the object P is set on the bed 37 in advance. Then, a static magnetic field is formed in the imaging region inside the static magnetic field magnet 21 (superconducting magnet) excited by the static magnetic field power supply 26. Additionally, electric current is supplied from the shim coil power supply 28 to the shim coil 22, thereby the static magnetic field formed in the imaging region is uniformed.

Next, in step 1, the imaging parameter determining unit 40B determines TI and a plurality of mutually different BBTIs of the time-SLIP sequence. These TI and BBTIs can be determined by performing a prescan or searching the database stored in the imaging parameter storing unit 40C.

In the case of determining TI and/or BBTIs by performing the prescan, the imaging conditions for the prescan are set in the imaging condition setting unit 40 in the way explained with FIG. 13. Then, the prescan is performed under ECG synchronization according to the imaging conditions set for the prescan. Moreover, TI and/or BBTIs are (is) determined based on the acquired blood flow images in the prescan. Additionally, in the case of determining TI and/or BBTIs by searching the database, the imaging parameter determining unit 40B obtains "TI and/or BBTIs corresponding to conditions inputted through the input device 33" from the imaging parameter storing unit 40C.

Next, in step 2, the time-SLIP sequence with the determined TI and the plurality of different BBTIs (see FIGS. 4 and 5) are set as imaging conditions for imaging in the imaging condition setting unit 40. Then, imaging without using a contrast medium is performed in synchronization with an ECG signal from the ECG unit 38 according to the set imaging conditions.

Concretely speaking, when imaging start command is inputted from the input device 33 to the sequence controller control unit 41, the sequence controller control unit 41 inputs the imaging conditions including the pulse sequence obtained from the imaging condition setting unit 40 to the sequence controller 31. The sequence controller 31 drives the gradient magnetic field power supply 27, the transmitter 29 and the receiver 30 in synchronization with the ECG signal from the ECG unit 38 according to the set pulse sequence so that a gradient magnetic field is formed in the imaging region where the object P is set and the RF coil 24 generates RF signals.

Therefore, NMR signals generated by nuclear magnetic resonance inside the object P are detected by the RF coil 24 and inputted to the receiver 30. The receiver 30 receives the NMR signals from the RF coil 24 and generates raw data. The receiver 30 inputs the generated raw data to the sequence controller 31. The sequence controller 31 inputs the raw data to the sequence controller control unit 41, and the sequence controller control unit 41 arranges the raw data in the k-space formed in the k-space database 42 as k-space data.

Note that the RMC is performed, if necessary, and data acquisition region is corrected according to the respiratory motion amount acquired based on the MPP.

Next, in step 3, the blood flow image generating unit 43 generates a plurality of image data corresponding to different BBTIs by obtaining the k-space data from the k-space database 42 and performing image reconstruction processing on the k-space data. Additionally, in the case of performing the RMC, phase of the k-space data or a position of the image data is corrected according to the respiratory motion amount acquired based on the MPP, if necessary.

Next, in step 4, the blood flow image generating unit 43 generates the plurality of blood flow image data corresponding to different BBTIs by performing necessary image processing such as differential processing on the reconstructed image data. The generated blood flow image data are stored in the image database 44. Moreover, the blood flow image generating unit 43 performs the base line correction on the image data so as to remove signal components of T1 recovery (longitudinal relaxation) of the background, if necessary. Note that the base line correction may be performed on the k-space data on which the image reconstruction processing has not been performed yet.

Next, in step 5, the blood flow information generating unit 45 generates the blood flow information on myocardial cross-sections based on the plurality of blood flow image data corresponding to different BBTIs and display the generated blood flow information on the display device 34. For example, a plurality of blood flow images corresponding to different BBTIs, profiles of signal intensity in myocardial cross-sections as shown in FIG. 16, a segment image of a myocardial cross-section indicating signal difference values corresponding to different BBTIs as shown in FIG. 17, and a curve of signal difference values as shown in FIG. 18 or 19 are displayed on the display device 34 as the blood flow information. Additionally, the positional correction of the blood flow image data is performed by using at least one of reference positions set to the border of the left and right ventricles as shown in FIG. 21, if necessary.

Therefore, a user can easily discover a lesion area such as an infarction area and an ischemia area, and can understand the range of the lesion area.

The magnetic resonance imaging apparatus 20 configured as mentioned above can acquire the blood flow information in a myocardium part without using a contrast medium in a cardiac study for an infarction part and an ischemia part. Specifically, the magnetic resonance imaging apparatus 20 performs spatial selective excitation so that signals of blood flowing into the imaging region set to myocardium part is distinguishable. In addition, the magnetic resonance imaging apparatus 20 changes the time from the region selective excitation to data acquisition. Thereby, the magnetic resonance imaging apparatus 20 generates a plurality of blood flow images indicating mutually different inflowing distance of blood.

Moreover, the magnetic resonance imaging apparatus 20 calculates the blood flow information such as a profile of the blood signal intensity and the blood signal difference values in a myocardial cross-section based on the plurality of blood flow image data indicating mutually different traveling distance of blood, and displays the blood flow information. Thereby, an infarction area and an ischemia area can be specified.

(Effect)

Therefore, according to the magnetic resonance imaging apparatus 20, there is no necessity of using a gadolinium contrast agent, and imaging can be performed with high resolution because there is no limit of data acquisition time. Concretely speaking, the magnetic resonance imaging apparatus 20 has several-fold in-plane resolution as compared with scintigraphy and perfusion examination in the conventional MRI. This is because the magnetic resonance imaging apparatus 20 performs 3-dimensional imaging. Therefore, resolution of a profile of blood signal improves and an infarction part and an ischemia part in myocardium can be depicted with high resolution.

Additionally, the magnetic resonance imaging apparatus 20 can depict natural flow of blood by a labeling method such as the time-SLIP method. Therefore, a blood flow image at an arbitrary time and a map of blood signal can be acquired. Moreover, the magnetic resonance imaging apparatus 20 can detect a lesion area such as an infarction part and an ischemia part based on time variation of blood signal and information on whether or not blood has moved on a blood flow image. In this case, the range of the lesion area can be distinguishably displayed with at least one of chromatic colors.

Moreover, there is no need to apply stress such as medication stress and exercise stress in the exemplary embodiments.

Additionally, micro-vascularity can be obtained by setting BBTI of the time-SLIP method, e.g., to 300 ms, 500 ms, 800 ms and 1000 ms. Then, the micro-vascularity can be observed by displaying profiles of blood signal or by displaying blood signal difference with bulls-eye display.

Additionally, the magnetic resonance imaging apparatus 20 can be used for screening study in comprehensive medical examination, because it can perform ischemia examination in myocardium without using a contrast medium.

(Modifications)

1. First Modification

In the aforementioned embodiment, an example of applying spatial selective 180° IR pulses as spatial selective excitation pulses for distinguishing signal of blood flowing into the imaging region is explained. However, the exemplary embodiments are not limited to such configuration. A 90° saturation pulse can be used as the spatial selective excitation pulse. When a 90° saturation pulse is applied as the spatial selective excitation pulse, a time interval from application timing of the 90° saturation pulse to start timing of data acquisition is set to a different value from the time interval in the case of applying the first and second spatial selective 180° IR pulse as the spatial selective excitation pulses (refer to FIGS. 4 and 5). For example, blood of unsaturated state flowing from the outside of the imaging region into the imaging region can be selectively emphasized, when imaging is performed under the following two conditions. That is, (A) the imaging region should be set to the entire myocardium and (B) the 90° saturation pulse should be applied to the same region as the imaging region with a changed time interval from the start timing of the data acquisition.

Additionally, for example, the data acquisition may be performed after applying the 90° saturation pulse as notched pulse without applying a spatial non-selective 180° IR pulse. That is, the 90° saturation pulse is applied as the notched pulse to the cardiac region exclusive of only the aorta (e.g., the region exclusive of only the "LABELED REGION" in FIG. 6 or 9). In this case, the signal level of the background can be inhibited, because the longitudinal magnetization component Mz of blood becomes zero in the region to which the notched pulse is applied. At the same time, the blood in the aorta without the influence of the notched pulse can be distinguished by performing data acquisition at an appropriate timing. This is because the longitudinal magnetization component Mz of the blood in the aorta without the influence of the notched pulse is one which is the same as the direction of the static magnetic field, and it inflows with high signal level into the imaging region.

2. Second Modification

In the aforementioned embodiment, an example of imaging under application of neither medicational stress nor exercise stress is explained. However, the exemplary embodiments are not limited to such configuration. Imaging may be performed applying both medication stress and exercise stress. Moreover, by performing the following two imaging sequences (X) and (Y) respectively, acquired blood flow images may be displayed in parallel so that blood flow images acquired in the imaging sequences (X) and (Y) can be compared with each other. In this case, both medicational stress and exercise stress or either one of them are (is) applied in the imaging sequence (X), whereas neither medicational stress or exercise stress is applied in the imaging sequence (Y). Additionally, blood flow image data for diagnosis can be generated and their images can be displayed by performing differential processing between "the blood flow image data acquired under application of stress to an object" and "the blood flow image data acquired without applying any stress to the object". By performing such comparative display and differential display, a patient is diagnosed more precisely.

3. Other Modification

In the aforementioned embodiment, an example of a setting pulse sequence by using an R wave of an ECG signal as a synchronization signal is explained with FIGS. 4 and 5. However, the exemplary embodiments are not limited to such configuration. The aforementioned PPG (peripheral pulse gating) signal or a cardiac sound synchronization signal may be acquired so that a pulse sequence is appropriately set based on the acquired signal.

Although an example of setting the imaging region to a heart is explained in the aforementioned embodiment, the blood flow image data can be acquired by setting the imaging region to a head or another organ except a heart, such as a kidney and a liver.

While certain embodiments have been described, these embodiments have been presented by way of example only, and are not intended to limit the scope of the exemplary embodiments. Indeed, the novel methods and systems described herein may be embodied in a variety of other forms; furthermore, various omissions, substitutions and changes in the form of the methods and systems described herein may be made without departing from the spirit of the exemplary embodiments. The accompanying claims and their equivalents are intended to cover such forms or modifications as would fall within the scope and spirit of the exemplary embodiments.

What is claimed is:

1. A magnetic resonance imaging (MRI) apparatus comprising:
an assembly of gantry components including static and gradient magnetic field generators and at least one radio frequency (RF) coil; and
an MRI control system, connected to control the gantry components, including at least one RF transmitter, at least one RF receiver and one or more computer control circuits, the MRI control system being configured to:
apply a spatially non-selective inversion pulse and a spatially selective excitation pulse, for distinguishably displaying inflowing blood flowing into an imaging region including myocardium;
acquire a plurality of imaging data sets without administration of a contrast medium, each of the plurality of imaging data sets corresponding to a respective one of a plurality of different traveling times of inflowing blood flowing into the imaging region in synchronization with a heartbeat together with delay times form synchronization signals, by changing a time from application timing of the spatially selective excitation pulse to acquisition timing of each of the plurality of imaging data sets, wherein the delay times are set such that the time from application timing of the spatially selective excitation pulse to acquisition timing of each of the plurality of imaging data sets spans multiple heart beats for at least one of the acquisitions of the plurality of imaging data sets; and
generate a plurality of blood flow image data sets, based on the acquired plurality of imaging data sets,
wherein the MRI control system is further configured to set the delay times so as to include a first delay time and a second delay time, the first delay time being a time interval from a first R-wave to an application time of the spatially non-selective inversion pulse, and the second delay time being a time interval from a second R-wave immediately before data acquisition to a start time of the data acquisition.

2. The magnetic resonance imaging (MRI) apparatus according to claim 1,
wherein the MRI control system is further configured to:
apply a labeling pulse as the spatially excitation pulse to a region different from the imaging region; and
acquire the plurality of imaging data sets for distinguishably displaying the inflowing blood labeled by the labeling pulse.

3. The magnetic resonance imaging (MRI) apparatus according to claim 2,
wherein the MRI control system is further configured to apply the labeling pulse to the region including a coronary artery.

4. The magnetic resonance imaging (MRI) apparatus according to claim 2,
wherein the MRI control system is further configured to apply the labeling pulse to the region including one of a right coronary artery (RCA), a left main coronary trunk (LMT), a left circumflex artery (LCX), and a left anterior descending artery (LAD), but not including the other three.

5. The magnetic resonance imaging (MRI) apparatus according to claim 2,
wherein the MRI control system is further configured to apply the labeling pulse to a slab set inside a ventricle.

6. The magnetic resonance imaging (MRI) apparatus according to claim 2,
wherein the MRI control system is further configured to:
apply the spatially non-selective inversion pulse to the imaging region, while applying the labeling pulse to the region different from the imaging region; and
acquire the plurality of imaging data sets, by further applying an imaging region selective inversion recovery pulse to excite the imaging region selectively after applying the spatially non-selective inversion pulse and the labeling pulse.

7. The magnetic resonance imaging (MRI) apparatus according to claim 2,
wherein the MRI control system is further configured to:
acquire the plurality of imaging data sets by applying the spatially non-selective inversion pulse to the imaging region, while applying the labeling pulse to the region different from the imaging region; and
set an inversion recovery time from application timing of the spatially non-selective inversion pulse to acquisition timing of the plurality of imaging data sets and a time interval from application timing of the labeling pulse to the acquisition timing of the plurality of imaging data sets, changeably and independently each other.

8. The magnetic resonance imaging (MRI) apparatus according to claim 1,
wherein the MRI control system is further configured to apply a further spatially selective excitation pulse between the application timing of the spatially selective excitation pulse and the acquisition timing of each of acquisitions of the plurality of imaging data sets.

9. The magnetic resonance imaging (MRI) apparatus according to claim 1,
wherein the MRI control system is further configured to generate the plurality of blood flow image data sets, by performing correction to eliminate a signal component corresponding to a background of an image from the plurality of imaging data sets.

* * * * *